(12) United States Patent
Bagnato et al.

(10) Patent No.: US 12,207,651 B2
(45) Date of Patent: Jan. 28, 2025

(54) APPARATUS AND METHODS FOR IRRADIATING ORGAN PERFUSATES

(71) Applicants: University Health Network, Toronto (CA); Universidade de São Paulo, São Paulo (BR)

(72) Inventors: Vanderlei Salvador Bagnato, São Carlos (BR); Marcelo Cypel, Toronto (CA); Shafique Keshavjee, Toronto (CA); Thomas Kenneth Waddell, Toronto (CA); Marcos Theophilo Galasso, Toronto (CA)

(73) Assignees: University Health Network, Toronto (CA); Universidade de Sao Paulo, Sao Paulo (BR)

( * ) Notice: Subject to any disclaimer, the term of this patent is extended or adjusted under 35 U.S.C. 154(b) by 963 days.

(21) Appl. No.: 16/500,657

(22) PCT Filed: Mar. 29, 2018

(86) PCT No.: PCT/CA2018/050400
§ 371 (c)(1),
(2) Date: Oct. 3, 2019

(87) PCT Pub. No.: WO2018/184100
PCT Pub. Date: Oct. 11, 2018

(65) Prior Publication Data
US 2020/0253195 A1    Aug. 13, 2020

Related U.S. Application Data

(60) Provisional application No. 62/481,523, filed on Apr. 4, 2017.

(51) Int. Cl.
*A01N 1/02* (2006.01)
*A61B 17/00* (2006.01)
(Continued)

(52) U.S. Cl.
CPC ......... *A01N 1/0294* (2013.01); *A01N 1/0247* (2013.01); *A61B 17/00* (2013.01);
(Continued)

(58) Field of Classification Search
None
See application file for complete search history.

(56) References Cited

U.S. PATENT DOCUMENTS

| 5,128,043 | A  | 7/1992 | Wildermuth |
| 6,447,720 | B1 | 9/2002 | Horton, III et al. |

(Continued)

FOREIGN PATENT DOCUMENTS

| CA | 2373673 C | 9/2011 |
| CN | 1320014 A | 10/2001 |

(Continued)

OTHER PUBLICATIONS

Galasso, M. et al., "Inactivating Hepatitis C Virus in Donor Lungs Using Light Therapies During Normothermic Ex Vivo Lung Perfusion." Nature Communications, 2019, 12 pages.

(Continued)

*Primary Examiner* — Andrew Smyth
(74) *Attorney, Agent, or Firm* — Morrison & Foerster LLP

(57) ABSTRACT

Disclosed are apparatuses and methods for irradiating a perfusate. The apparatus includes a tank which defines a first chamber. A separator is located inside the first chamber. The separator defines a second chamber. The first chamber and the second chamber are concentric and have substantially annular cross sections, each having at least one diameter and a substantially common longitudinal axis. A perfusate is introduced into the first chamber by an inlet. A UV radiation-emitting device is disposed inside the second chamber for providing irradiation to the perfusate. Irradiated perfusate is removed from the tank by an outlet. Other apparatuses and systems are described and methods for inactivating micro organisms by performing EVP and irradiating the perfusate.

13 Claims, 24 Drawing Sheets

(51) Int. Cl.
A61L 2/00 (2006.01)
A61L 2/10 (2006.01)
A61L 2/24 (2006.01)
A61L 2/26 (2006.01)

(52) U.S. Cl.
CPC .............. *A61L 2/0047* (2013.01); *A61L 2/10* (2013.01); *A61L 2/24* (2013.01); *A61L 2/26* (2013.01); *A61B 2017/00969* (2013.01); *A61L 2202/11* (2013.01); *A61L 2202/121* (2013.01); *A61L 2202/122* (2013.01); *A61L 2202/14* (2013.01); *A61L 2202/182* (2013.01)

(56) References Cited

U.S. PATENT DOCUMENTS

| | | | | |
|---|---|---|---|---|
| 6,899,355 | B2* | 5/2005 | Klein | F16L 33/227 285/259 |
| 6,972,415 | B2 | 12/2005 | Schaible et al. | |
| 7,425,272 | B2* | 9/2008 | Butters | C02F 1/325 210/748.14 |
| 7,687,045 | B2* | 3/2010 | Lu | A61L 2/20 219/679 |
| 7,888,656 | B2 | 2/2011 | Freedgood | |
| 7,993,580 | B2 | 8/2011 | Anderle | |
| 2003/0049809 | A1* | 3/2003 | Kaiser | A23L 3/28 422/24 |
| 2007/0202485 | A1 | 8/2007 | Nees et al. | |
| 2010/0056643 | A1 | 3/2010 | Bachynsky et al. | |
| 2014/0334974 | A1* | 11/2014 | Rasooly | A61L 2/10 250/455.11 |
| 2018/0070583 | A1 | 3/2018 | Paul et al. | |
| 2019/0033419 | A1* | 1/2019 | Golay | G01R 33/30 |
| 2020/0138015 | A1 | 5/2020 | Bagnato et al. | |

FOREIGN PATENT DOCUMENTS

| | | | |
|---|---|---|---|
| CN | 1565654 A | 1/2005 | |
| CN | 100369633 C | 2/2008 | |
| CN | 101360522 A | 2/2009 | |
| CN | 102241427 A | 11/2011 | |
| CN | 102361823 A | 2/2012 | |
| CN | 204910182 U | 12/2015 | |
| WO | 1988/005261 A1 | 7/1988 | |
| WO | WO-8805261 A * | 7/1988 | .............. A01N 1/02 |
| WO | 2016/090498 A1 | 6/2016 | |
| WO | 2016/207335 A1 | 12/2016 | |

OTHER PUBLICATIONS

Khan, B. et al., "Successful Lung Transplantation From Hepatitis C Positive Donor to Seronegative Recipient." American Journal of Transplantation, 2017, vol. 17, pp. 1129-1131.

Inci, I. et al., "Ex Vivo Reconditioning of Marginal Donor Lungs Injured by Acid Aspiration." The Journal of Heart and Lung Transplantation, 2008, vol. 27, No. 11, pp. 1229-1236.

Nakajima, D. et al., "Lung Lavage and Surfactant Replacement During Ex Vivo Lung Perfusion for Treatment of Gastric Acid Aspiration-Induced Donor Lung Injury." The Journal of Heart and Lung Transplantation, 2017, vol. 36, No. 5, pp. 577-585.

Machuca, T.N. et al., "Lung Transplantation With Donation After Circulatory Determination of Death Donors and the Impact of Ex Vivo Lung Perfusion." DCDD Lung Transplantation and EVLP. American Journal of Transplantation, 2015, vol. 15, No. 4, pp. 993-1002.

Machuca, T.N. et al., "Injury-Specific Ex Vivo Treatment of the Donor Lung: Pulmonary Thrombolysis Followed by Successful Lung Transplantation." American Journal of Respiratory and Critical Care Medicine, 2013; vol. 188, No. 7, pp. 878-880.

Mohr, H. et al., "A Novel Approach to Pathogen Reduction in Platelet Concentrates Using Short-Wave Ultraviolet Light." Transfusion, 2009, vol. 49, No. 12, pp. 2612-2624.

Steinmann, E. et al., "Two Pathogen Reduction Technologies-Methylene Blue Plus Light and Shortwave Ultraviolet Light-Effectively Inactivate Hepatitis C Virus in Blood Products." Transfusion, 2013, vol. 53, No. 5, pp. 1010-1018.

Floyd, R. A. et al., "Methylene Blue Photoinactivation of RNA Viruses." Antiviral Research, 2004, vol. 61, No. 3, pp. 141-151.

Müller-Breitkreutz, K, et al., "Hepatitis C and Human Immunodeficiency Virus RNA Degradation By Methylene Blue/Light Treatment of Human Plasma." Journal of Medical Virology, 1998, vol. 56, No. 3, pp. 239-245.

Bachmann, B. et al., "Target Structures for HIV-1 Inactivation by Methylene Blue and Light." Journal of Medical Virology, 1995, vol. 47, No. 2, pp. 172-178.

Smith, D. B. et al., "Variation of the Hepatitis C Virus 5' Non-Coding Region: Implications for Secondary Structure, Virus Detection and Typing." Journal of General Virology, 1995, vol. 76, No. 7, pp. 1749-1761.

Wakita T., "Isolation of JFH-1 Strain and Development of an HCV Infection System." Hepatitis C: Methods and Protocols, Second Edition, vol. 510, Humana Press, 2009, pp. 305-327.

Extended European Search Report dated Mar. 15, 2021, directed to EP Application No. 18780312.7; 11 pages.

International Search Report and Written Opinion dated Jun. 12, 2018, directed to International Application No. PCT/CA2018/050400; 14 pages.

Notification of The First Office Action dated Oct. 14, 2020, directed to CN Application No. 201880030158.X; 18 pages.

European Patent Application No. EP18780312, Supplementary Partial European Search Report, dated Dec. 2, 2020, 4 pages.

Examination Report No. 1 dated Jun. 30, 2022, directed to AU Application No. 2018247584; 6 pages.

Bagnato et al., U.S. Office Action mailed Jan. 18, 2023, directed to U.S. Appl. No. 16/593,314; 14 pages.

Bagnato et al., U.S. Office Action mailed Oct. 24, 2023, directed to U.S. Appl. No. 16/593,314; 20 pages.

Bagnato et al., U.S. Office Action dated May 24, 2024, directed to U.S. Appl. No. 16/593,314; 21 pages.

* cited by examiner

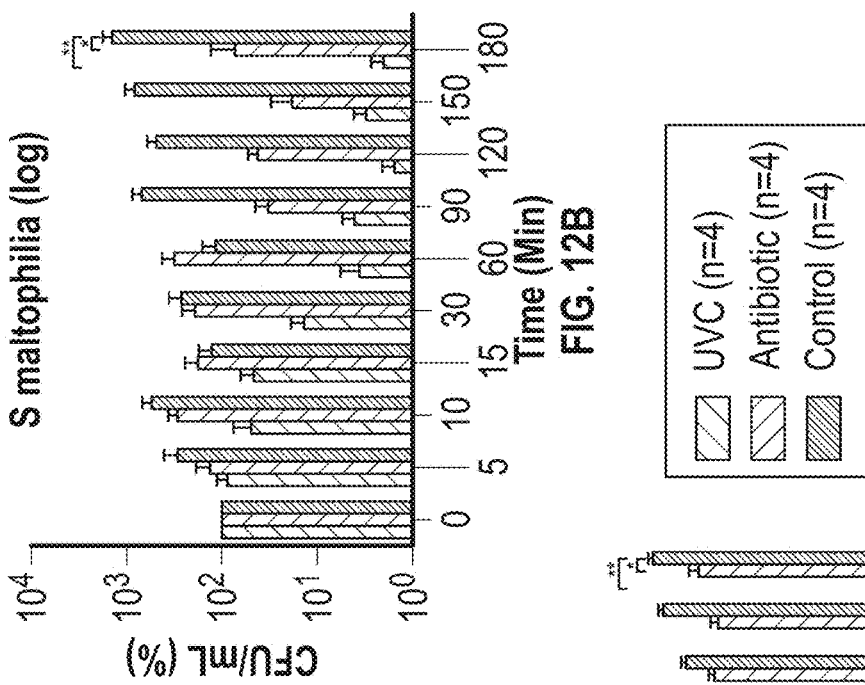
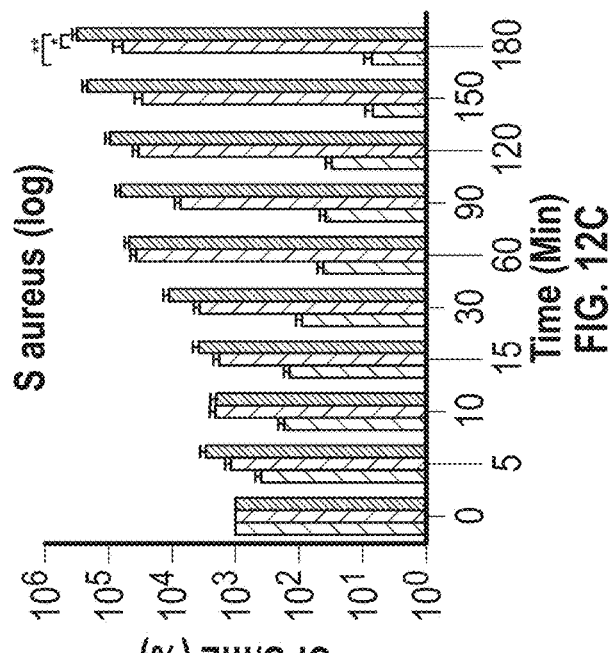
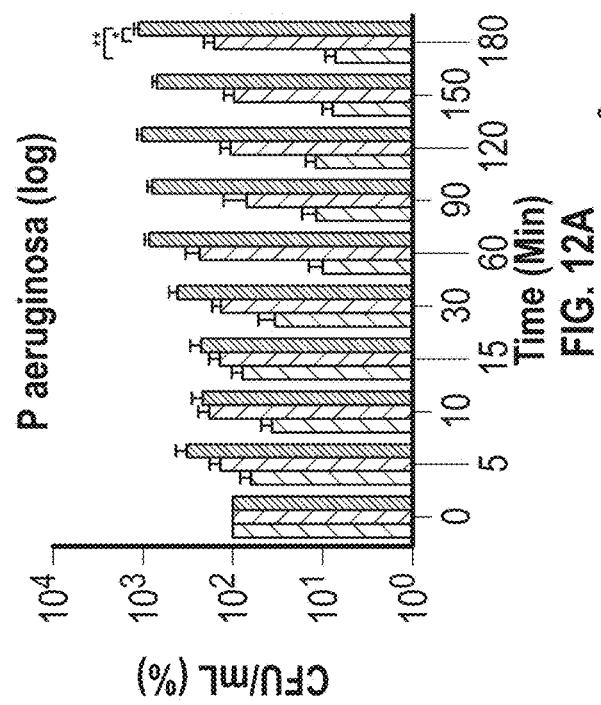
FIG. 12A
FIG. 12B
FIG. 12C

FIG. 15B

APPARATUS AND METHODS FOR IRRADIATING ORGAN PERFUSATES

CROSS-REFERENCE TO RELATED APPLICATION

This application is a U.S. national stage application under 35 U.S.C. § 371 of International Application No. PCT/CA2018/050400, filed Mar. 29, 2018, which claims the benefit of U.S. Provisional Patent Application No. 62/481,523, filed on Apr. 4, 2017. The entire contents of each priority application are incorporated herein by reference.

INTRODUCTION

Field of the Invention

The present invention relates generally to systems and methods for inactivating microorganisms, preferably viruses, such as one or more of HCV virus, HIV, Hepatitis B, Cytomegalovirus (CMV), Epstein-Barr virus, (EBV), and adenovirus or bacteria such as staphylococcal bacteria, e.g. *Staphylococcus aureus, Stenotrophomonas maltophilia*, and a pseudomonad bacteria e.g. *Psuedomonas aeruginosa* in donor organs such as lungs using ex vivo perfusion and UV irradiation or photodynamic treatment (PDT).

BACKGROUND

There is an insufficient number of suitable donor organs to satisfy the growing wait lists of patients requiring transplantation.

For example, lung transplantation is lifesaving for patients with end-stage lung diseases. However, the number of patients waiting for a lung transplant greatly exceeds the number of available donors. Further, the end-stage lung disease patient list is growing.

It is estimated that 130-150 million chronic Hepatitis C patients worldwide (which is about 2% North America). Hepatitis C virus positive (HCV+) donors are generally not offered for lung transplantation because the risk of transmission to recipients is greater than 90%. Direct-acting antiviral drugs (DAA) may be useful to treat donor recipients after viral transmission from HCV+ donor lungs (Khan B et al. Am J Transplant 2017. Doi: 10.1111/ajt.14137). Adding HCV+ donors to the list could represent about 1,000 new donors in North America per year.

Decreasing hepatitis C virus (HCV) viral load and/or inactivating virus present in donor lungs could increase organ availability.

Decreasing viral or bacterial load present in other organs could similarly increase availability of other organs.

Ex vivo perfusion is used with donor kidneys has also been used with other organs such as lungs and hearts.

Ex vivo lung perfusion (EVLP) for example is a method for assessing lung viability and/or treating lungs before transplantation. Strategies such as EVLP have been used to treat damaged donor lungs due to aspiration pneumonia, pulmonary edema and pulmonary embolism as described in Inci I, Ampollini L, Arni S, et al. Ex vivo reconditioning of marginal donor lungs injured by acid aspiration. *The Journal of Heart and Lung Transplantation.* 2008; 27(11):1229-1236; Nakajima D, Liu M, Ohsumi A, et al. Lung Lavage and Surfactant Replacement During Ex Vivo Lung Perfusion for Treatment of Gastric Acid Aspiration-Induced Donor Lung Injury. *The Journal of Heart and Lung Transplantation.* 2017; 36(5):577-585. doi:10.1016/j.healun.2016.11.010; Machuca T N, Mercier O, Collaud S, et al. Lung Transplantation With Donation After Circulatory Determination of Death Donors and the Impact of Ex Vivo Lung Perfusion: DCDD Lung Transplantation and EVLP. *American Journal of Transplantation.* 2015; 15(4):993-1002. doi:10.1111/ajt.13124 and Machuca T N, Hsin M K, Ott H C, et al. Injury-specific ex vivo treatment of the donor lung: pulmonary thrombolysis followed by successful lung transplantation. *American journal of respiratory and critical care medicine.* 2013; 188(7):878-880. With EVLP, lungs are perfused and ventilated ex vivo at body temperature to mimic physiologic conditions.

Methods for inactivating microorganisms using light sources are known in the art. For example, U.S. Pat. No. 7,993,580 discloses a method of using monochromatic or polychromatic light emitted from one or more light sources to effectively inactivate microorganisms present in a biological fluid in a batch reactor. As another example, U.S. Ser. No. 10/196,020 discloses providing a UV reactor, in the form of an elongated generally annular reaction chamber surrounding at least one elongated UV lamp, moving a biological fluid within the reaction chamber in a primary flow directed along the length of the UV lamp, and inducing a circulating secondary flow within the fluid with the secondary flow being superimposed on the primary flow. As a further example, U.S. Pat. No. 6,447,720 teaches a system for ultraviolet disinfection of a fluid wherein the ultraviolet light source is submerged in the fluid, and wherein untreated influent enters the system flowing past the submerged light source and exits the output as treated disinfected effluent.

Photodynamic therapy (PDT) is another light-based therapy used for blood components sterilization in blood banks (Mohr H, Steil L, Gravemann U, et al. BLOOD COMPONENTS: A novel approach to pathogen reduction in platelet concentrates using short-wave ultraviolet light: UVC IRRADIATION FOR PATHOGEN REDUCTION IN PCs. *Transfusion.* 2009; 49(12):2612-2624. doi:10.1111/j.1537-2995.2009.02334.x; Steinmann E, Gravemann U, Friesland M, et al. Two pathogen reduction technologies-methylene blue plus light and shortwave ultraviolet light-effectively inactivate hepatitis C virus in blood products: INACTIVATION OF HCV IN BLOOD PRODUCTS. *Transfusion.* 2013; 53(5):1010-1018. doi:10.1111/j.0537-2995.2012.03858.x; Floyd R A, Schneider Jr. J E, Dittmer D P. Methylene blue photoinactivation of RNA viruses. *Antiviral Research.* 2004; 61(3):141-151. doi:10.1016/j.antiviral.2003.11.004 and Müller-Breitkreutz K, Mohr H. Hepatitis C and human immunodeficiency virus RNA degradation by methylene blue/light treatment of human plasma. *Journal of medical virology.* 1998; 56(3):239-245. PDT involves administration of a drug, called photosensitizer, which requires light irradiation in a specific wavelength to be activated, being transformed from a stable state (ground state) to an excited stated (singlet state), followed by a decay phase, in which Reactive Oxygen Species (ROS) are formed. This therapy results in a sequence of photobiological processes that cause irreversible photodamage to viruses, including HCV and HIV-1 (Bachmann B, Knüver-Hopf J, Lambrecht B, Mohr H. Target structures for HIV-1 inactivation by methylene blue and light. *Journal of medical virology.* 1995; 47(2):172-178; Bachmann B, Knüver-Hopf J, Lambrecht B, Mohr H. Target structures for HIV-1 inactivation by methylene blue and light. *Journal of medical virology.* 1995; 47(2):172-178).

It is an objective of the present invention to decrease pathogen load and/or inactivate microorganisms in a donor organ optionally a donor lung by treating perfusate of the donor organ with light therapy. It is an objective of the present invention to decrease and/or inactivate microorganisms, preferably viruses such as one or more of HCV virus, HIV, Hepatitis B, Cytomegalovirus (CMV), Epstein-Barr virus, (EBV), and adenovirus or bacteria such as one or more of a staphylococcal bacteria, e.g. *Staphylococcus aureus*, *Stenotrophomonas maltophilia*, and a pseudomonad bacteria e.g. *Psuedomonas aeruginosa*, in a donor organ using ex vivo perfusion.

SUMMARY

The following summary is intended to introduce the reader to the more detailed description that follows, and not to define or limit the claimed subject matter.

According to an aspect, the present subject matter relates to an irradiation apparatus comprising:
- a tank defining a first chamber;
- a separator located inside the first chamber, the separator defining a second chamber wherein the first chamber and the second chamber are concentric and have substantially annular cross sections, each having at least one diameter and a substantially common longitudinal axis;
- an inlet by which perfusate is introduced into the first chamber;
- an outlet by which irradiated perfusate in the first chamber is removed from the tank; and
- a radiation-emitting device disposed inside the second chamber for providing irradiation to the perfusate.

According to another aspect, the present subject matter relates to an irradiation apparatus for irradiating an organ perfusate. In one embodiment, the apparatus comprises:
- a tank defining a first chamber;
- an inlet by which the perfusate is introduced into the first chamber;
- an outlet by which irradiated perfusate in the first chamber is removed from the tank;
- a separator located inside the first chamber and defining a second chamber, the separator forming a barrier between the second chamber from the first chamber; and
- a UV radiation-emitting device disposed inside the second chamber for providing irradiation to the perfusate.

In one embodiment, the perfusate is lung perfusate.

In one embodiment, the radiation-emitting device is a UV radiation device.

In one embodiment, the radiation-emitting device is a UVC lamp.

In another embodiment, the separator is made of quartz glass.

In a further embodiment, the tank is made of glass.

In one embodiment, a plastic external protection having an annular cross section is applied to the external surface of the tank.

According to another aspect, there is disclosed an irradiation apparatus comprising
- a lower unit;
- an upper unit pivotally mounted on the lower unit such that the upper unit is moveable the lower unit to open and close the apparatus;
- at least one radiation source mounted on one of the lower and upper units;
- wherein the upper and lower units define a chamber for receiving a receptacle, and wherein each of the side panels of the lower unit defines a groove adapted to support a body portion of the receptacle. In one embodiment, the at least one radiation source comprises an ultraviolet lamp.

In another embodiment, the ultraviolet lamp comprises one of: ultraviolet-A lamp, ultraviolet-B and ultraviolet-C.

In a further embodiment, the irradiation apparatus further comprises safety sensors for detecting when the upper unit is moved up and/or down on top of the lower unit, such that the sensors detect when the apparatus is open and/or closed and for preventing it from being inadvertently activated while the apparatus open.

In one embodiment, the safety sensors comprise sensing plates positioned on the lower and upper units, such that the sensors detect when the upper unit and the lower unit are not in contact.

According to another aspect, there is disclosed a quartz tube comprising
- an elongate tubular body comprising an external surface, the body having an inlet and outlet, and
- gripping means machined on the external surface at ends of the inlet and outlet for providing a snuggly fit when the quartz tube is connected to external tubes.

In one embodiment, a sterile package comprises the quartz tube as described above In another embodiment, the sterile package further comprises a connector adapted to connect to the quartz tube and external tubing.

According to one aspect, there is disclosed an irradiation system comprising:
- an irradiation apparatus and a receptacle;
- the irradiation apparatus comprising
  - a lower unit and an upper unit pivotally mounted on the lower unit such that the upper unit is moveable with respect to the lower unit to open and close the apparatus;
  - at least one radiation source mounted on one of the lower and upper units;
  - wherein the upper and lower units define a chamber for receiving a receptacle and each side panel of the lower unit defines a groove adapted to support a body portion of the receptacle;
- the receptacle comprising an inlet by which a solution can be introduced into the receptacle; and an outlet by the solution can be removed therefrom, wherein gripping means are machined at ends of the inlet and outlet for providing a snuggly fit when the receptacle is connected to external tubes.

In one embodiment, the at least one radiation source comprises an ultraviolet lamp.

In another embodiment, the ultraviolet lamp comprises one of: ultraviolet-A lamp, ultraviolet-B and ultraviolet-C or a lamp that emits red light, optionally a red light lamp, or a light source that comprises red light.

In a further embodiment, the irradiation apparatus further comprises safety sensors for detecting when the upper unit is moved up and/or down on top of the lower unit, such that the sensors detect when the irradiator is open and/or closed and for preventing the apparatus from being inadvertently activated while the apparatus is in an open configuration.

In one embodiment, the safety sensors comprise sensing plates positioned on the lower and upper units, such that the sensors detect when the upper unit is moved on top of the lower unit.

According to a further aspect, the present subject matter relates to a method for decreasing and/or inactivating microorganisms, including viruses and bacteria in a donor organ prior to transplant, the method comprising: performing ex vivo perfusion (EVP) on a donor organ using a perfusion solution to produce a perfusate; and irradiating the perfusate using for example an irradiation apparatus as described herein.

In one embodiment, the donor organ is a donor lung and the EVP is ex vivo lung perfusion (EVLP).

In one embodiment, the irradiation is UVC irradiation. In an embodiment, the irradiation comprises or consists of red light irradiation.

The irradiation is optionally performed for a portion of the EVP or during the entire time of the EVP.

In an embodiment, the method comprises performing standard EVP on the donor organ performed for at least or about 2 hours, at least or about 4 hours, at least or about 6 hours, at least or about 8 hours or at least or about nine hours, optionally up to or about 18 hours.

In an embodiment, the irradiation is performed for at least two and up to 18 hours, optionally up to 15 hours, up to 12 hours, up to 9 hours, up to 6 hours or up to 4 hours, optionally for a same period as the EVP.

In another embodiment, a photosensitizer such as methylene blue is added to the perfusion solution and the irradiation comprises or consists of red light irradiation. Any virucidal/bactericidal photosensitizer can be used in combination with the activating light.

In some embodiments, the perfusate or a portion of the perfusate is exchanged with perfusion solution during the EVP and the method comprises performing a second EVP on the donor organ. For example, the first EVP can be performed for about 1 hour, about 2 hours, about 3 hours and the second EVP is performed for about 1 to 6 hours.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

DRAWINGS

For a better understanding of the embodiments described herein and to show more clearly how they may be carried into effect, reference will now be made, by way of example only, to the accompanying drawings which show at least one exemplary embodiment, and in which:

FIG. 12A is a graph showing effect of UVC and antibiotic on levels of P. aeruginosa in perfusate.

FIG. 12B is a graph showing effect of UVC and antibiotic on levels of S. malophilia in perfusate.

FIG. 12C is a graph showing effect of UVC and antibiotic on levels of S. aureus in perfusate.

FIG. 15B is a series of graphs showing PCR detection of HCV.

Figure 16:
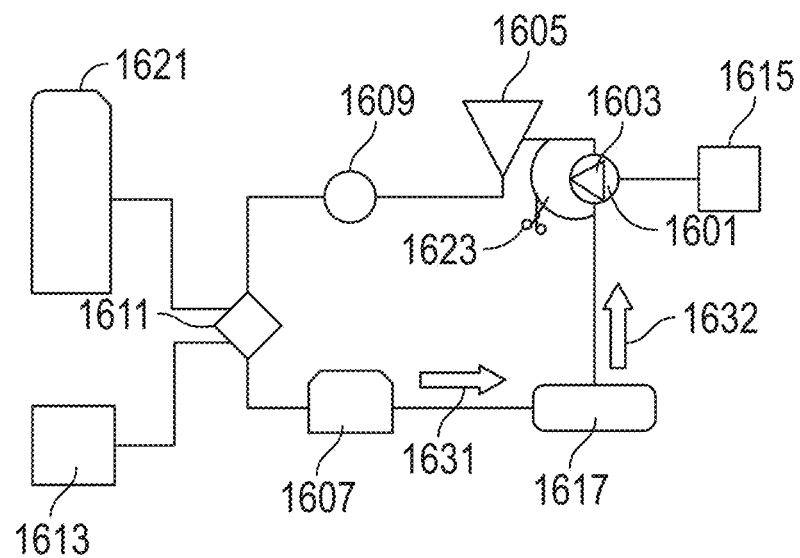

FIG. 16, there is shown a block diagram of an EVLP system.

Figure 17:
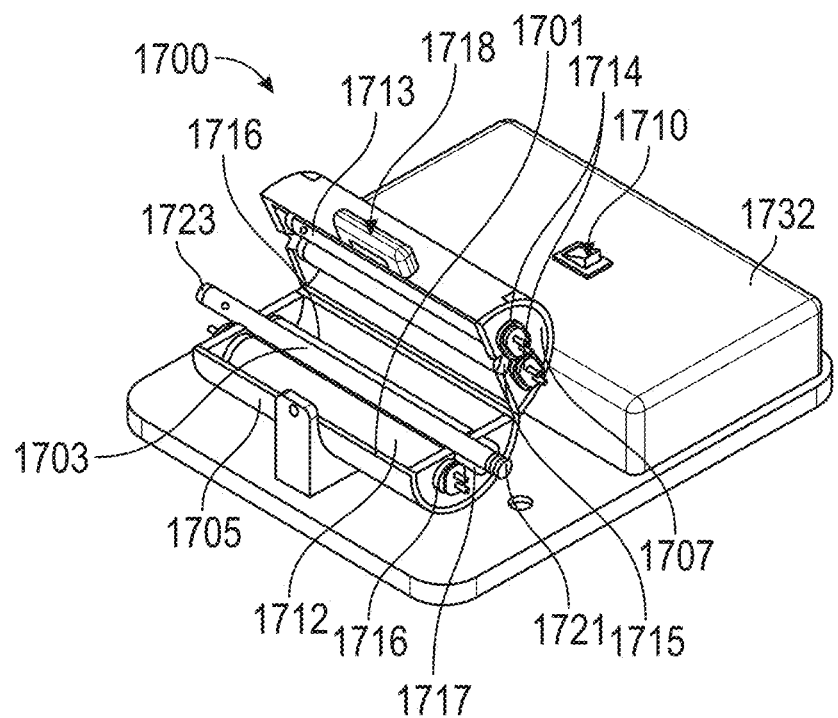

FIG. 17 illustrates a diagram of an irradiation system.

Figure 18:
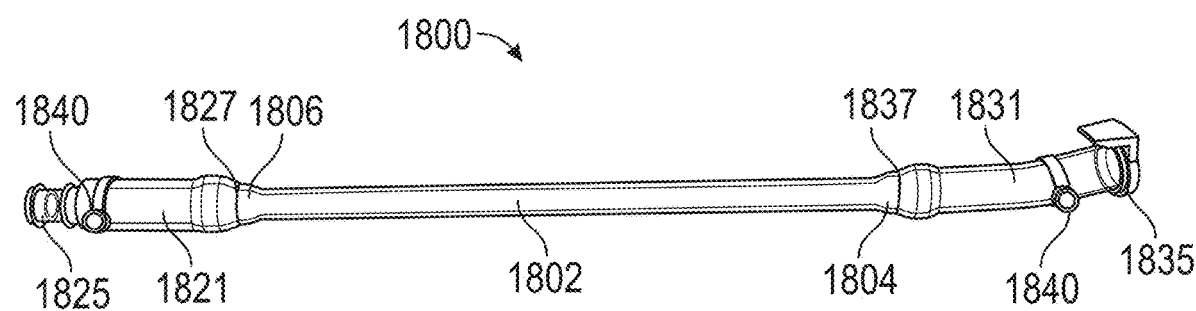

FIG. 18 illustrates an exemplary embodiment of a quartz tube.

FIGS. 19A, 19B, 19C and 19D illustrate an exemplary embodiment of an irradiation system.

DESCRIPTION OF PARTICULAR EMBODIMENTS

Described herein are irradiators for irradiating a perfusate in an ex vivo perfusion (EVP) system. It is demonstrated herein that light therapies such as UVC and photodynamic therapy (PDT) using for example methylene blue can be used with EVP by treating the perfusate circulating through an organ in the EVP circuit to inactivate virus and bacteria in an infected organ rendering the organ safe for transplant.

The term "EVP" or "ex vivo perfusion" refers to perfusion of a donor organ that has been harvested from a donor and includes for example normothermic EVP and hypothermic EVP. When the EVP is lung EVP, it is referred to as EVLP, when the EVP is kidney EVP it can be referred to as EVKP, when the EVP is cardiac/heart EVP, it can be referred to as EVCP and when the EVP is hepatic/liver EVP it can be referred to as EVHP.

The term "standard EVP" as used herein involves pumping a nutrient solution (i.e. perfusion solution) such as Steen Solution™ with or without an oxygen carrier through the blood vessels of the donor organ, for lengths of time and under conditions known in the art. Depending on the organ, the EVP may comprise organ specific components. For example, for a lung, oxygen is supplied by a ventilator machine. For example, the term "standard EVLP" as used herein involves pumping a nutrient solution (i.e. perfusion solution) such as Steen Solution™ (XVIVO) through the blood vessels of the lungs while at the same time supplying them with oxygen from a ventilator machine.

The term "perfusion solution" as used herein means any solution that is used to perfuse an organ. For example, Steen Solution™ is commonly used for EVP including EVLP although other lung perfusion solutions have also been described, for example as disclosed in US Patent Application 20180070583. The perfusion solution may contain an oxygen carrier such as a red blood cell concentrate, blood such as whole blood, an acellular hemoglobin-based oxygen carrier (HBOC), or HBOC plus plasma (HBOC+Plasma), for example in addition to STEEN Solution (XVIVO Perfusion, Goteborg, Sweden). Oxygen carriers may be used for example when the donor organ is a heart, kidney or liver.

The term "perfusate" as used herein means a perfusion solution that has been or is being used for ex vivo perfusion e.g. perfusion solution that has been pumped through an organ at least once, such as in lung, kidney, heart or liver EVP.

The term "lung perfusate" as used herein means a perfusion solution such as Steen Solution™ that is used for EVLP that has been pumped through a lung. Similarly, a "kidney perfusate" as used herein means a perfusion solution that is used for EVKP that has been pumped through a kidney etc.

The term "Steen Solution™" as used herein means a buffered dextran containing extracellular-type solution with an optimized colloid osmotic pressure developed specifically for EVLP, containing Human Serum Albumin, Dextran and extra-cellular electrolyte composition (lowK+). The Steen solution may be acellular as typically in EVLP and/or comprise in addition an oxygen carrier.

Terms of degree such as "about", "substantially", and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

Unless otherwise defined, scientific and technical terms used in connection with the present disclosure shall have the meanings that are commonly understood by those of ordinary skill in the art. Further, unless otherwise required by context, singular terms shall include pluralities and plural terms shall include the singular.

In the following description, specific details are set out to provide examples of the claimed subject matter. However, the embodiments described below are not intended to define or limit the claimed subject matter.

It will be appreciated that, for simplicity and clarity of illustration, where considered appropriate, reference numerals may be repeated among the figures to indicate corresponding or analogous elements or steps. Numerous specific details are set forth in order to provide a thorough understanding of the exemplary embodiments of the subject matter described herein. However, it will be understood by those of ordinary skill in the art that the embodiments described herein may be practiced without these specific details. In other instances, well-known methods, procedures and components have not been described in detail so as not to obscure the present subject matter. Furthermore, this description is not to be considered as limiting the scope of the subject matter in any way but rather as illustrating the various embodiments.

Figure 1A:
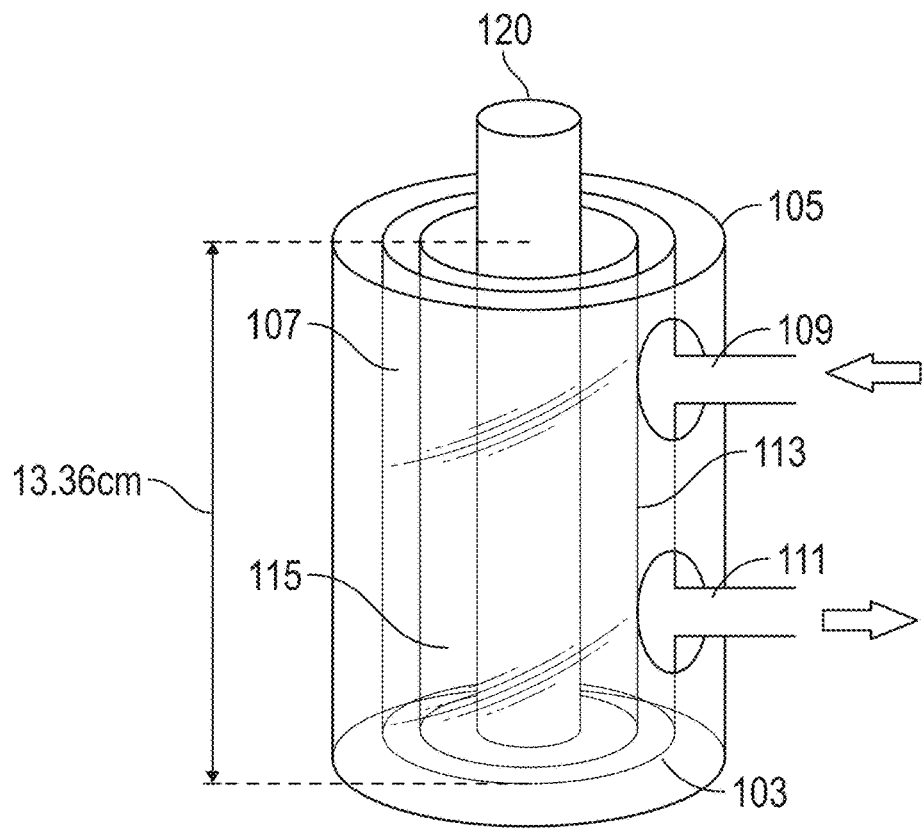
FIG. 1A is an illustration of an apparatus for irradiating a perfusate.
Figure 1B:
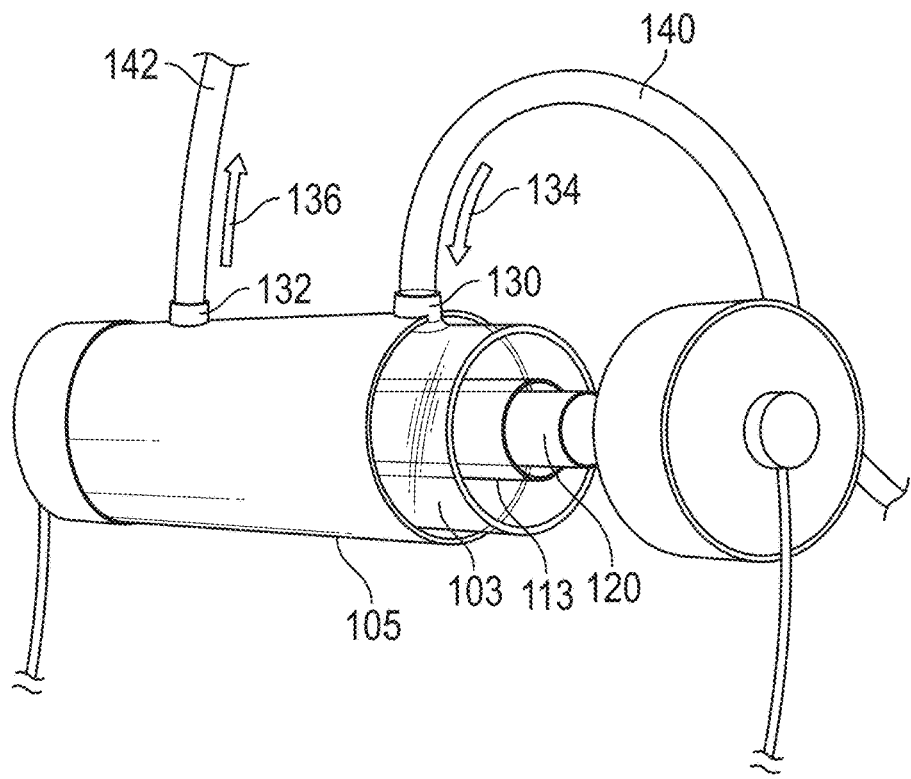
FIG. 1B is a perspective illustration of the apparatus of FIG. 1A

As shown on FIGS. 1A and 1B, apparatus for irradiating a solution (i.e. perfusion solution/perfusate, optionally referred to as a perfusate) has a tank 103 defining an interior chamber. The tank may be upright and its height may be greater than its span. The tank may be made of glass, or other suitable material. The tank may have a generally circular cross-section. In one embodiment, the tank diameter may be between 2 to 5 centimeters. The tank may also have the cross section of a polygon, such as a quadrilateral, a pentagon, a hexagon, a heptagon or an octagon.

As shown on FIGS. 1A and 1B, a plastic external protection 105 is applied to the external surface of the tank 103. The plastic external protection may take the shape of the tank. The plastic external protection may have a generally circular cross-section. In one embodiment, the radius of the plastic external protection may be between 3 to 6 centimeters. For example, the radius of the plastic external protection may be about 3.8, or optionally 3.77 centimeters.

The tank 103 defines an interior chamber 107 with an upper portion and a lower portion. The upper part of the tank may generally be cylindrical. The lower portion of the tank 101 may generally be cylindrical.

The tank 103 has a feed inlet 109. The feed inlet 109 introduces perfusate that comes from an organ into the upper portion of the chamber 107. The tank 103 may comprise one or more feed inlets to introduce the perfusate into the chamber 107. The feed inlet 109 may include an elbow that directs the perfusate downwardly into the upper portion of the chamber. The feed inlet 109 may further include an elbow that directs the perfusate upwardly into the upper portion of the chamber. The flow of the perfusate passing through the feed inlet 109 may range between 1 to 3 liters per minute depending on the organ size, in a constant flow.

In one embodiment, the flow rate is 1.5 liters per minute to ensure constant flow in the organ and/or accommodate the organ size. In another embodiment, the flow rate is 2 liters per minute to ensure constant flow in the organ and/or accommodate the organ size. In a further embodiment, the flow rate is 2.5 liters per minute to ensure constant flow in the organ and/or accommodate the organ size.

In some embodiments, the perfusate is a lung perfusate. In one embodiment, the flow rate is 1.5 liters per minute to ensure constant flow in the lung and/or accommodate the lung size. In another embodiment, the flow rate is 2 liters per minute to ensure constant flow in the lung and/or accommodate the lung size. In a further embodiment, the flow rate is 2.5 liters per minute to ensure constant flow in the lung and/or accommodate the lung size.

The tank 103 comprises an outlet 111 by which the perfusate is removed from the tank 103. The outlet may be located in the lower portion of the chamber. The perfusate that is removed from the tank 103 at the outlet 111 is irradiated. The tank may comprise one or more outlets to remove irradiated perfusate from the chamber 107.

A separator 113 defines a second chamber 115 inside the chamber 107. The separator may extend along a longitudinal axis of the tank. The second chamber 115 may have a cylindrical shape. A radiation emitting device, optionally a UV radiation-emitting device 120 is disposed inside the second chamber 115. The radiation emitting device, optionally a UV radiation-emitting device may provide irradiation to the perfusate that flows in the chamber 107. The separator 113 keeps the second chamber 115 apart from the chamber 107. The separator 113 operates as a barrier between the second chamber 115 and the chamber 107. The radiation emitting device may also be a red light emitting device.

In one embodiment, the chamber 107 and the second chamber 115 are concentric and have substantially annular cross sections, each having at least one diameter and a substantially common longitudinal axis.

In one embodiment, a circular hollow cylinder is formed inside the first chamber 107. The circular hollow cylinder is a three-dimensional region bounded by the two concentric cylindrical sections of the first and second chamber and two parallel annular bases of the tank. The two parallel annular bases may be perpendicular to the cylinder's axis. When the perfusate enters the tank 103, the perfusate is contained inside the circular hollow cylinder. Once inside the circular hollow cylinder, the perfusate passes around the radiation-emitting device located inside the second chamber 115. The perfusate may have a constant flow inside the circular hollow cylinder.

Figure 2:
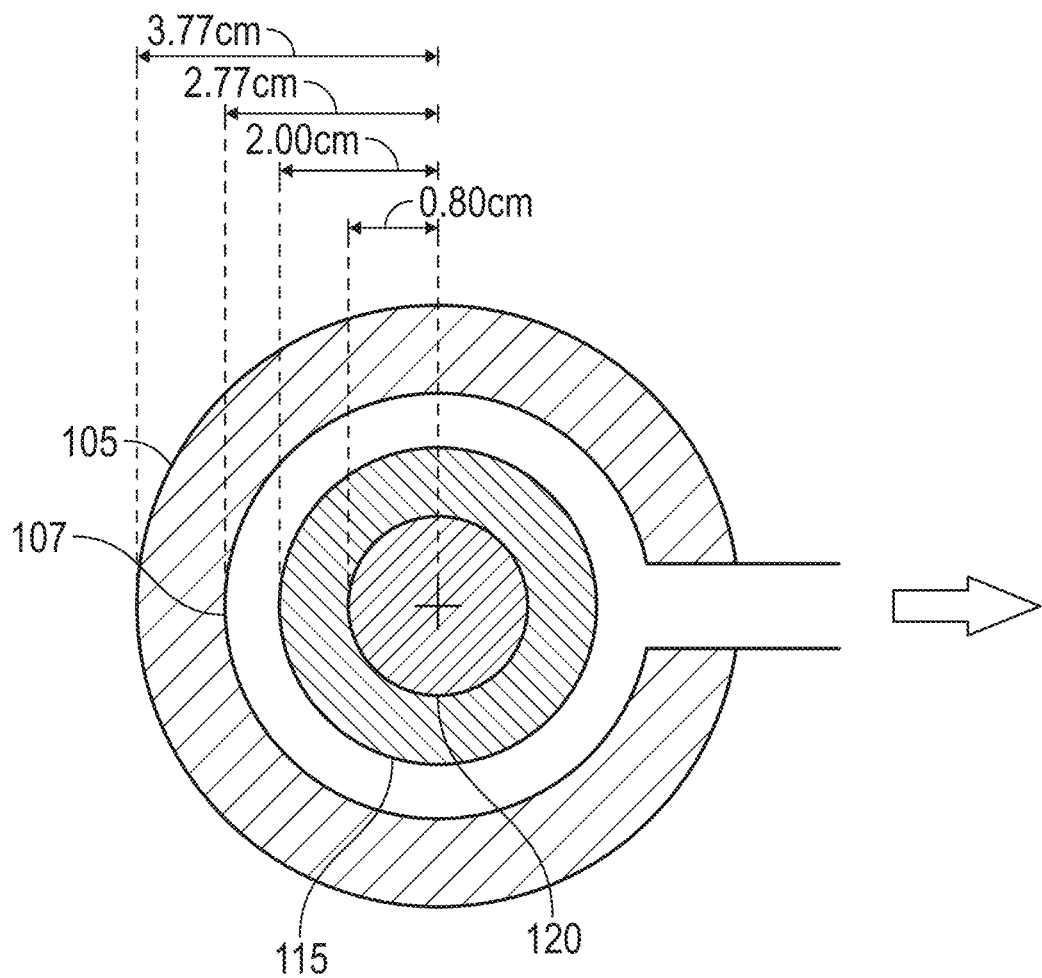
FIG. 2 is a cross sectional view of the apparatus of FIG. 1A.

FIG. 2 shows a cross sectional view of an exemplary embodiment of the apparatus for irradiating a perfusate. The chamber 107 and the second chamber 115 are concentric and have substantially annular cross sections. The radius of the chamber 107 may be about 2.8 centimeters, optionally 2.77 centimeters. The radius of the second chamber 115 may be about 2 centimeters. The plastic external protection is also concentric to the first and second chamber. For example, the radius of the plastic external protection 105 may be about 3.8 centimeters, optionally 3.77 centimeters.

The length of the common longitudinal axis may be between 10 to 20 centimeters. Returning to FIG. 1A, the length of the common longitudinal axis may be about 13.3 centimeters, optionally 13.36 centimeters. As the perfusate flows in the chamber 107, a radiation-emitting device disposed inside the second chamber provides irradiation to the perfusate.

The separator 113 may be made of quartz glass, or other suitable material. The optical and thermal properties of quartz glass are superior to those of other types of glass due to its purity. For example, the low coefficient of thermal expansion of quartz glass makes it a useful material for forming a barrier between a radiation-emitting device and the chamber containing the perfusate. Quartz glass as a separator may have a wide transparency range, which extends from the ultraviolet (UV) to the near infrared (IR). Because of its strength and high melting point (compared to ordinary glass), quartz glass is used as an envelope for the radiation-emitting device.

For example, the UV radiation-emitting device may be a UVC radiation device. For example, the UV radiation-emitting device may be an ultraviolet C (UVC) lamp. The UV radiation-emitting device may have a cylindrical shape with substantially an annular cross section. The red light radiation emitting device may similarly have a cylindrical shape with substantially an annular cross section.

Figure 3:
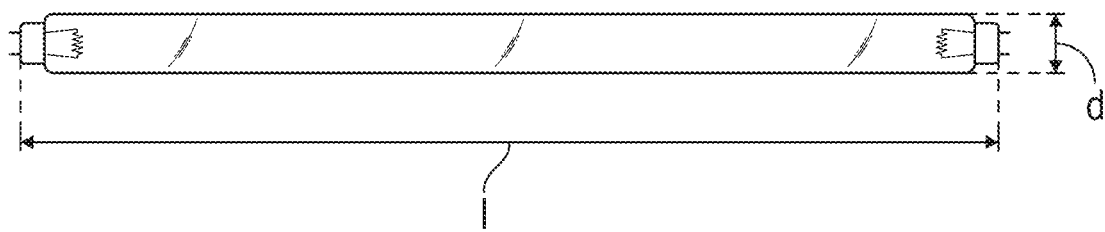
FIG. 3 is an illustration of a UV radiation-emitting device.

FIG. 3 shows an exemplary embodiment of a UV radiation-emitting device. The diameter of the device may be about 1.6 centimeters. The longitudinal length of the device may be about 13.4 centimeters, optionally 13.36 centimeters.

Returning to FIG. 2, there is shown a radiation emitting device such as a UV radiation-emitting device 120 inside the second chamber 115. In this embodiment, the UV radiation-emitting device 120 is concentric to the second chamber 115. The radius of the UV radiation-emitting device 120 can be about 0.8 centimeters.

In operation, perfusate enters the irradiation apparatus through the feed inlet (or solution input). The perfusate is a nutrient solution which as a result of perfusing the organ can contain microorganisms, for example viruses such as one or more of HCV virus, HIV, Hepatitis B, Cytomegalovirus (CMV), Epstein-Barr virus, (EBV), and adenovirus and/or bacteria such as one or more of a staphylococcal bacteria, e.g. *Staphylococcus aureus, Stenotrophomonas maltophilia*, and pseudomonad bacteria e.g. *Psuedomonas aeruginosa*. The perfusate enters the irradiation apparatus at a controlled flow rate. Irradiated perfusate may exit the irradiation apparatus at the same flow rate. The controlled flow rate may be between 0.1 to 3 liters per minute. For example, the lung perfusate may enter the irradiation apparatus at a flow rate of 1.5 liters per minute. As another example, the perfusate may enter the irradiation apparatus at a flow rate of 2 liters per minute. As a further example, the perfusate may enter the irradiation apparatus at a flow rate of 2.5 liters per minute. The perfusion flow rate is selected based on the organ size.

Once in the irradiation apparatus, the perfusate is typically exposed to continuous irradiation e.g. UVC light from a UV radiation-emitting device or red light from a red light emitting device for a minimum period of time. For example, the UV radiation-emitting device may be a UVC lamp. The UVC lamp may emit electromagnetic radiation with a wavelength from 100 nm to 280 nm. For example, the UVC lamp emits electromagnetic radiation at a wavelength of 253.7 nm. The UVC lamp bulb may transmit energy at a rate of 0.9 Joules per second (or Watt). The radiant intensity of the UVC lamp may be 450 µW/cm2 (where µW=10−6 J/sec). The red light emitting device may be a red light lamp and provide red light of about 620 nm to about 750 nm, particularly emitting wavelengths 620 nm to 640 nm.

Referring to FIG. 17, there is illustrated a diagram of an irradiation system 1700 for providing irradiation to a solution. For example, the solution can be a perfusate. The irradiation system 1700 includes an irradiator 1701 and an (irradiation) receptacle 1703. For example, the irradiation system can irradiate a solution in a manner such that a precisely controllable dose of irradiation is efficiently delivered to the solution.

Referring back to FIG. 17, the irradiator 1701 includes a lower unit 1705 and an upper unit 1707. For example, the lower unit can be a base. For example, the upper unit is pivotally mounted to the lower unit, such that the upper unit is moveable with respect to the lower unit to open and close the irradiator. A holder 1718 can be used to open and close the upper unit.

Within at least one and preferably each of the lower unit 1705 and upper unit 1707, is/are radiation sources 1712 and 1713, for example, the radiation source can be a lamp. For example, the irradiator can include one or more reactors, optionally four reactors. For example, a reactor include a power unit and the radiation source such as, for example, one or more lamps (or bulbs). For example, the lamps can be elongated and/or tubular. For example, a bivolt (127 V/220 V) AC power cord can be connected to a power outlet to power to the reactors.

For example, two lamps can be installed in the lower unit. For example, two lamps can installed in the upper unit. For example, when the irradiator is in a closed position, the upper and lower units form a chamber. For example, a solution to be irradiated is pumped into or otherwise moves through the chamber through the receptacle where it can be exposed to radiation such as UV light from the lamps. The chamber can have a predetermined width.

For example, the lamp can be an Ultraviolet-A (UV-A) lamp for providing UV-A light. For example, the UV-A lamp can emit a light of about 320 nm to about 400 nm. For example, the lamps can be Ultraviolet-B (UV-B) lamps for providing UV-B light. For example, the UV-B lamp can emit a light of about 290 nm to about 320 nm. The lamp can also for example be a red light lamp and provide red light of about 620 nm to about 750 nm, particularly including 620 nm to 640 nm.

For example, the irradiator is equipped with four UV lamps or 4 red light lamps for providing irradiation. For example, the lower and upper units of the irradiator can each be equipped with two UV-C lamps. For example, UV-C lamps can be mounted on platforms of the lower and upper units. For example, the UV-C lamps can operate with a voltage at about 29 volts, a current at about 0.17 amps and a power at about 4 watts. For example, the lamps can be parallel. For example, the lamps can be elongate and tubular.

For example, the lower and upper units can contain a plurality of lamps for providing an even irradiation to a solution inside the receptacle (e.g. tube) within the irradiator. For example, the irradiator can contain at least two lamps for providing an even exposure to irradiation. For example, the irradiator can be a platform containing four low pressure mercury UVC lamps (operating at 254 nm) operating at 4 W. For example, each lamp can delivers 31 mW/cm$^2$ optical power density when in contact with a quartz tube, with approximately 24 mW/cm$^2$ in the center of the quartz tube per lamp. For example, this represents a total of approximately 96 mW/cm$^2$ in the center of the quartz tube when four lamps are used together.

For example, when the irradiator is in a closed position, the upper and lower units form a chamber and encloses the lamps. For example, the upper unit is pivotally mounted on the lower unit such that the upper unit is moveable with respect to the lower unit to open and close the irradiator. For example, the upper and lower units define a chamber for receiving a receptacle. For example, side panels of the lower unit define a groove adapted to support a body portion of the receptacle.

Referring back to FIG. 17, the lower unit 1705 has side panels 1716 on each side of the lower unit. Each side panel defines a groove 1717 upon which the receptacle 1703 can be supported during the irradiation process. The upper unit 1707 has side panels 1714 on each side of the upper unit and each side panel that defines a groove 1715 for accommodating a body portion of the receptacle during irradiation. For example, grooves 1715 and 1717 define a side opening in the side panels 1714 and 1716 when the irradiator is in a closed position. For example, the lamp(s) on the lower unit 1705 and the upper unit 1707 can define a cavity that accommodates the receptacle. For example, the cavity is a gap or volume between the lower and upper units. For example, the receptacle is placed in such gap during the irradiation process.

For example, a disposable quartz tube can be placed inside the cavity to feed a solution (e.g. a perfusate) to be decontaminated by the irradiator. For example, the disposable quartz tube can be placed adjacent to or in contact with the lamps when inserted in the cavity.

For example, the irradiator can be equipped with one lamp for providing irradiation. For example, the irradiator can be equipped with two or more lamps for providing irradiation. For example, the lamps can be easily replaceable. For example, the lamps can be removed from the irradiator, such as the lamps are removable or detachable from the upper and lower units. For example, a user can remove UV-B lamps from the irradiator and replace them with UV-C lamps or UV-A lamps. For example, a lamp can include an outer sleeve and a lamp circuit having at its ends sockets or connector members by which electric current is supplied to the lamp. Examples of lamps include mercury vapor lamp capable of producing ultraviolet light. It should be understood by those skilled in the art that any number of irradiation lamps can be employed to provide irradiation inside to the irradiator. For example, the irradiator can be designed to achieve a desired rate of solution throughput while also ensuring that proper irradiation doses are received.

For example, the lamps can be Ultraviolet-A (UV-A) lamps for providing UV-A light. For example, the UV-A lamp can emit a light of about 320 nm to about 400 nm. For example, the lamps can be Ultraviolet-B (UV-B) lamps for providing UV-B light. For example, the UV-B lamp can emit a light of about 290 nm to about 320 nm. For example, the lamps can be Ultraviolet-C (UV-C) lamps for providing UV-C light. For example, the UV-Clamp can emit a light of about 100 nm to about 280 nm. For example, the irradiator can be equipped with four UV-C lamps for providing irradiation. For example, the lower and upper units of the irradiator can each be equipped with two UV-C lamps. In other embodiments, the lamps are red light lamps and provide red light of about 620 nm to about 750 nm, particularly including wavelengths 620 nm to 640 nm.

For example, when the irradiator is in a closed position, the upper and lower units form a irradiation chamber. For example, a solution to be irradiated is pumped into or otherwise moves through the chamber through the receptacle where it can be exposed to UV light from the lamps. For example, the receptacle can be a quartz tube. For example, the quartz the lamps can be touching the quartz inside the radiation chamber. For example, the quartz tube can be at a short distance of the lamps. For example, the quartz tube can be placed adjacent to the lamps.

For example, a lamp can have a diameter of 16 mm. For example, a lamp can have a diameter of about 12 mm to about 20 mm. For example, a lamp can have a diameter of about 8 mm to about 24 mm. For example, a lamp can have a length of 136 mm. For example, a lamp can have a length of about 130 mm to about 142 mm. For example, a lamp can have a length of about 124 mm to about 152 mm. For example, a lamp can have a length of about 118 mm to about 158 mm.

For example, a lamp can produce a fluence of 31 mW/cm$^2$. For example, a lamp can produce a fluence of about 25 mW/cm$^2$ to about 37 mW/cm$^2$. For example, a lamp can produce a fluence of about 19 mW/cm$^2$ to about 43 mW/cm$^2$. For example, a lamp can produce a fluence of about 13 mW/cm$^2$ to about 49 mW/cm$^2$.

For example, the lamps can pulse red light or UV rays (such as UV-A rays, UV-B rays and UV-C rays) at a frequency between 1 and 200 Hz and have a duration of between one nanosecond and one second. For example, the frequency of the pulses is about 50 Hz. For example, the duration of the pulses can be about 2 milliseconds.

Referring back to FIG. 17, an On/Off button 1710 is shown on the irradiator. For example, the On/Off button 1710 can be placed on a control unit of the irradiator.

Figure 19A:
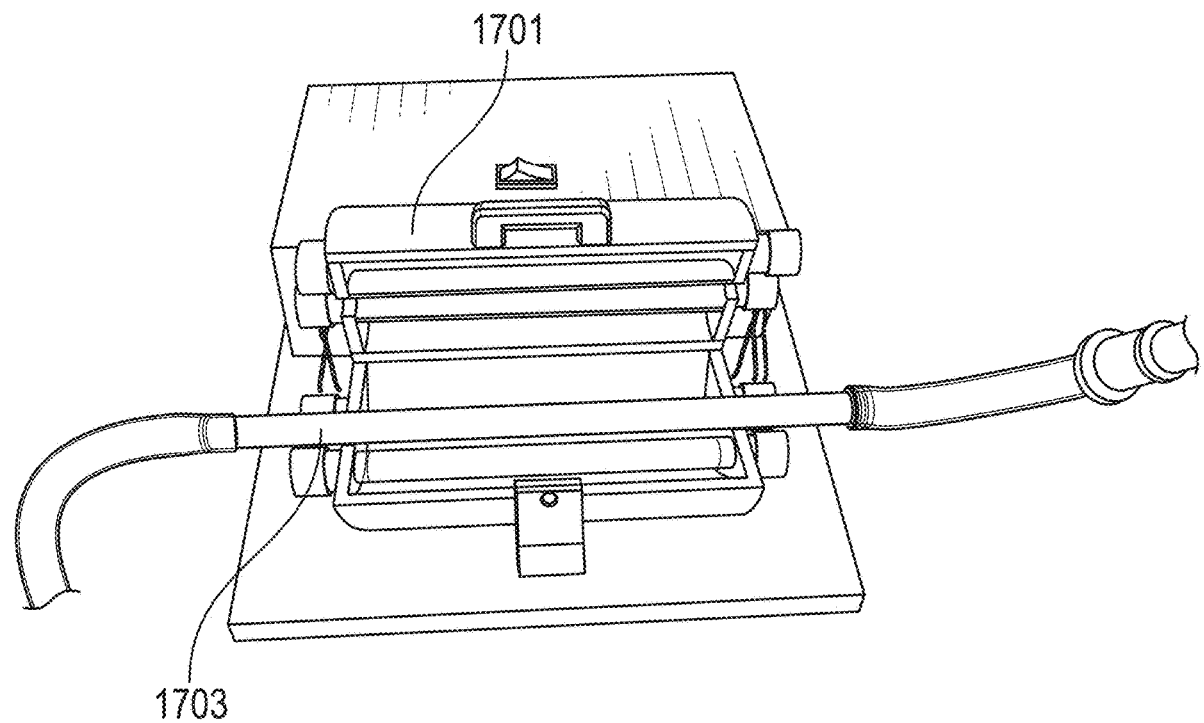
Figure 19B:
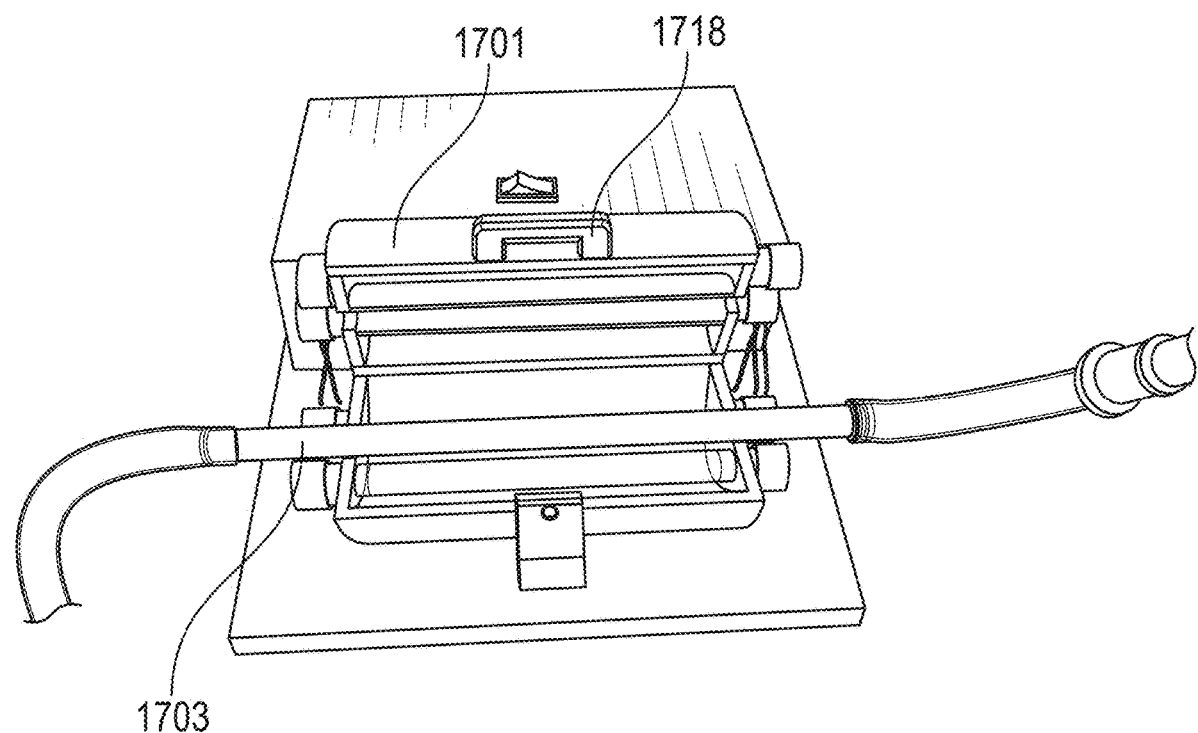
Figure 19C:
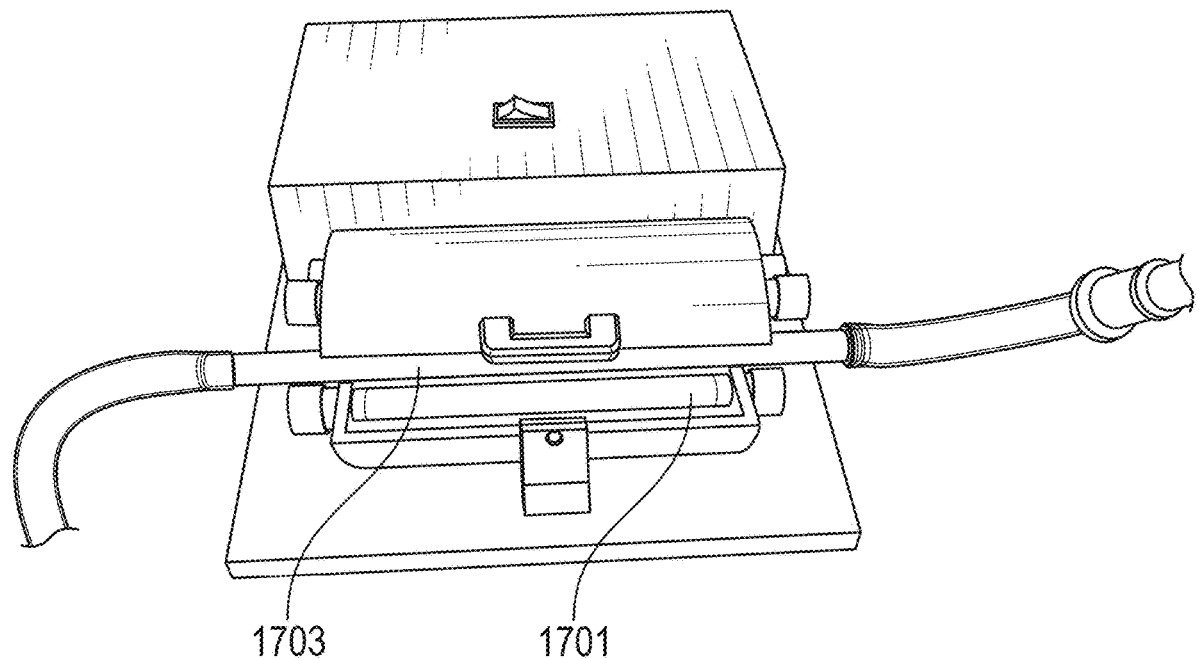
Figure 19D:
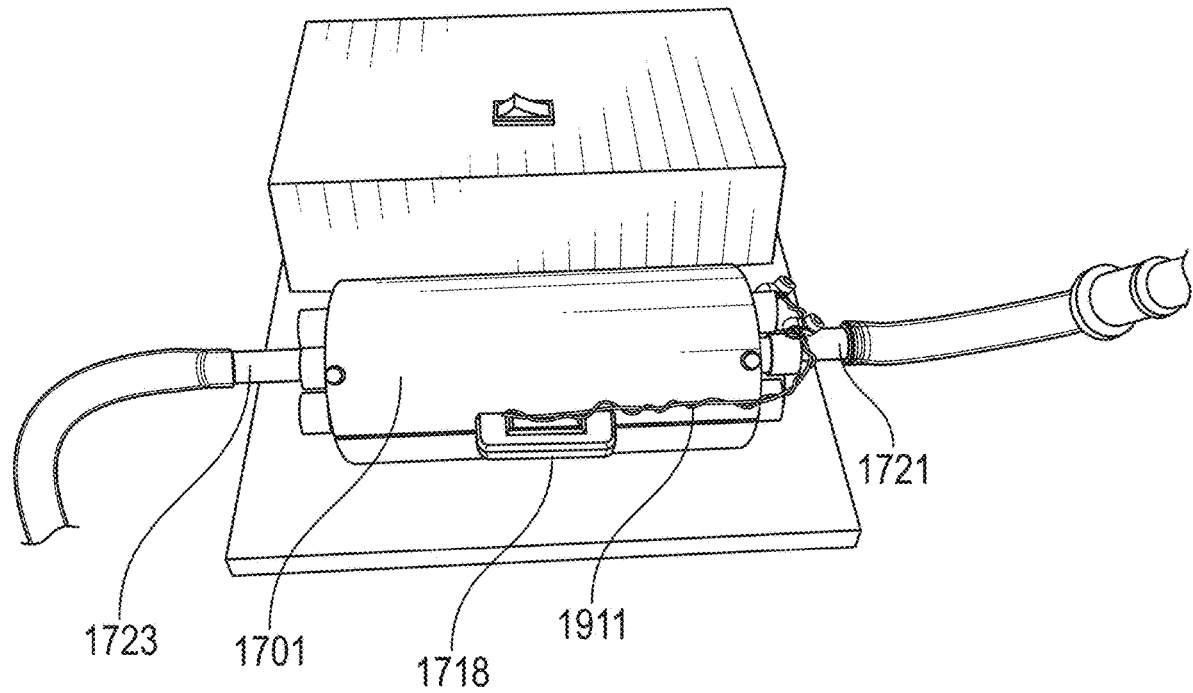

Referring to FIGS. 19A, 19B, 19C and 19D, a receptacle 1703 is placed in the cavity inside an irradiator 1701. An inlet 1723 and an outlet 1721 of the receptacle are shown at FIG. 19D. For example, the receptacle can be a quartz tube. In FIGS. 19A and 19B, the irradiator 1701 is an open position. For example, the quartz tube can also be connected to an EVP system. An inlet of the quartz tube can be connected to an outlet of the EVP system and an outlet of the quartz can be connected to an inlet of the EVP system. As shown in FIGS. 19B and 19C, a user is in the process of closing the irradiator 1701 by using the holder 1718. In FIG. 19D, the irradiator 1701 is closed as the upper unit is resting on top of the lower unit. It is also shown a cable 1911 that connects to the safety sensors for detecting when the irradiator is open and/or closed. The cable can be connected to a control unit of the irradiator, which controls the operation of the device. For example, the safety sensors can detect when the upper unit is in close contact with the lower unit, such that the sensors detect when the apparatus is open and/or closed. For example, the sensors can prevent the apparatus from being inadvertently activated while the apparatus is open.

For example, when the irradiator is turned on, the lamps generate an electron beam or other comparable irradiation beam that is directed into the quartz tube to irradiate the solution inside the quartz tube, as the solution is flowing inside the quartz tube from the inlet to the outlet. For example, irradiation is provided along the entire external surface of the quartz tube. As the perfusion solution flowing through the quartz tube is being irradiated, irradiated perfusion solution exits the quartz tube through its outlet.

For example, the irradiator includes safety sensors for detecting when the upper unit is moved up and/or down on top of the lower unit, such that the sensors detect when the irradiator is open and/or closed. For example, the irradiator can have safety sensors that prevents it from being inadvertently activated while the upper unit is open. When the irradiator is open, the sensor turns OFF the lamps and/or prevent them from emitting radiation that would otherwise potentially be harmful and present a hazard to operating personnel.

For example, the sensors can be structures consisting of two pairs of parallel sensing plates for detecting when the irradiator is in an open and/or closed position. For example, each pair of plates can be placed on the lower and upper units respectively, such that the sensors detect when the upper unit is moved on top of the lower unit. Thus, the sensors detect when the upper unit is open and/or closed.

Referring back to FIG. 17, there is shown an irradiation receptacle 1703. For example, the irradiation receptacle can be a tube. For example, the irradiation receptacle can be a quartz tube. The receptacle 1703 has an inlet 1723 by which a solution is introduced into the receptacle. For example, the solution can be a solution (e.g. a perfusate/perfusion solution, a Steen™ solution, etc.). The receptacle 1703 has an outlet 1721 by which irradiated solution can be removed therefrom.

For example, microorganisms inactivation in a solution can occurs when the receptacle is being irradiated by the irradiator and the solution circulates through the receptacle, allowing the irradiation of the solution by UV light or red light. For example, the solution in the receptacle flows near the light source along a circulation path. The light source is optionally a UV light source or a red light source. For example, the UV light source can be a UV-A lamp(s). For example, the UV light source can be a UV-B lamp(s). For example, the UV light source can be a UV-C lamp(s).

Referring to FIG. 18, there is shown a quartz tube 1800 having an elongate tubular body including an external surface 1802. The quartz tube 1800 has an inlet 1806 by which a solution is introduced into the quartz tube. The receptacle 1800 has an outlet 1804 by which solution can be removed therefrom. For example, gripping means can be machined on the external surface at ends of the inlet and outlet for providing a snuggly fit when the quartz tube is connected to external tubes.

For example, the quartz tube can have a length of 133 mm. For example, the quartz tube can have a length of about 100 mm to about 170 mm. For example, the quartz tube can have a length of about 70 mm to about 200 mm. For example, the quartz tube can have a length of about 30 mm to about 240 mm.

For example, the quartz tube can be sold as a single piece. For example, the quartz can be sold in a sterile package. For example, the quartz can be easily sterilized.

Referring back to FIG. 17, the receptacle 1703 can be a quartz tube as described in FIG. 18. The receptacle has gripping means 1723A at the inlet 1723 and gripping means 1721A at the outlet 1721. For example, the gripping means can be machined into the inlet and outlet of the receptacle. The gripping means can be used to provide a snuggly fit when they are connected to a connector or tube.

For example, the receptacle/quartz tube can be connected in series to a system (such as an EVP system, an EVLP system, an EVKP system, an EVCP system, an EVHP system). For example, the tube(s) of such system can be connected to the quartz tube by using male/female connectors. For example, the male/female connectors can be made of PVC. For example, the male and female connectors can define an elongate piece defining a central passage with two opposite ends.

Referring back to FIG. 18, a male connector 1821 is connected to the inlet 1806 of the quartz tube. The male connector 1821 has a female plug-receiving opening 1825 at one end and a tube receiving opening 1827 at the other end. A female connector 1831 is connected to the outlet 1804 of the quartz tube. The female connector 1831 has a male plug-receiving opening 1835 at one end and a tube receiving opening 1837 at the other end. For example, the female plug-receiving opening is adapted to receive the male plug-receiving opening when the male and female connectors are connected (not shown).

The male and female connectors includes a stop-flow button/pin 1840 for stopping the flow of fluid inside the connectors. The fluid flow inside the connector(s) can be stopped when connecting the connectors to the quartz tube and/or a system tubing.

As shown in FIG. 18, the male connector 1821 is connected to the quartz tube 1800 as the inlet 1806 is fitted into the tube receiving opening 1827. The female connector 1831 is connected to the quartz tube 1800 as the outlet 1804 is fitted into the tube receiving opening 1837.

For example, the male and/or female connector(s) can be sold as a single piece. For example, a connector can be sold in a sterile package.

For example, the quartz tube can be sold with one or more connectors. For example, a sterile package can comprise a quartz tube with one or more connectors.

For example, the quartz tube can have a wall thickness of 21.6 mm. For example, the quartz tube can have a wall thickness of about 18.6 mm to about 24.6 mm. For example, the quartz tube can have a wall thickness of about 15.6 mm to about 27.6 mm. For example, the quartz tube can have a wall thickness of about 12.6 mm to about 30.6 mm.

For example, the flow rate of solution, which passes through the quartz tube, can be 1 L/min. For example, the flow rate of solution can be about 0.8 L/min to about 1.2 L/min. For example, the flow rate of solution can be about 0.6 L/min to about 1.4 L/min. For example, the flow rate of solution can be about 0.4 L/min to about 1.6 L/min.

For example, the temperature inside the irradiator and the receptacle (e.g. tube) during irradiation can be 37° C. For example, the temperature can be about 35° C. to about 39°. For example, the temperature can be about 33° C. to about 41°. For example, the temperature can be about 30° C. to about 44°.

For example, the quartz tube can be replaceable. For example, the quartz tube can be sterilized easily. For example, the quartz tube can be used as a vitreous envelope material. For example, the quartz tube can withstand high operating temperatures of up to about 1100° C. In some embodiments the quartz tube.

For example, the receptacle can be connected to an EVP system, optionally an EVLP system, such as the EVLP system described in FIG. 16. For example, the receptacle can be connected at various points of the EVP system for providing irradiation to the perfusion solution/perfusate.

The irradiator apparatuses and systems described herein can be used for example with EVLP, EVKP, EVCP and EVHP.

Accordingly, the perfusate can be a lung perfusate, a kidney perfusate, a heart perfusate, a liver perfusate or a perfusate from any organ that may be perfused prior to transplantation.

Figure 4:
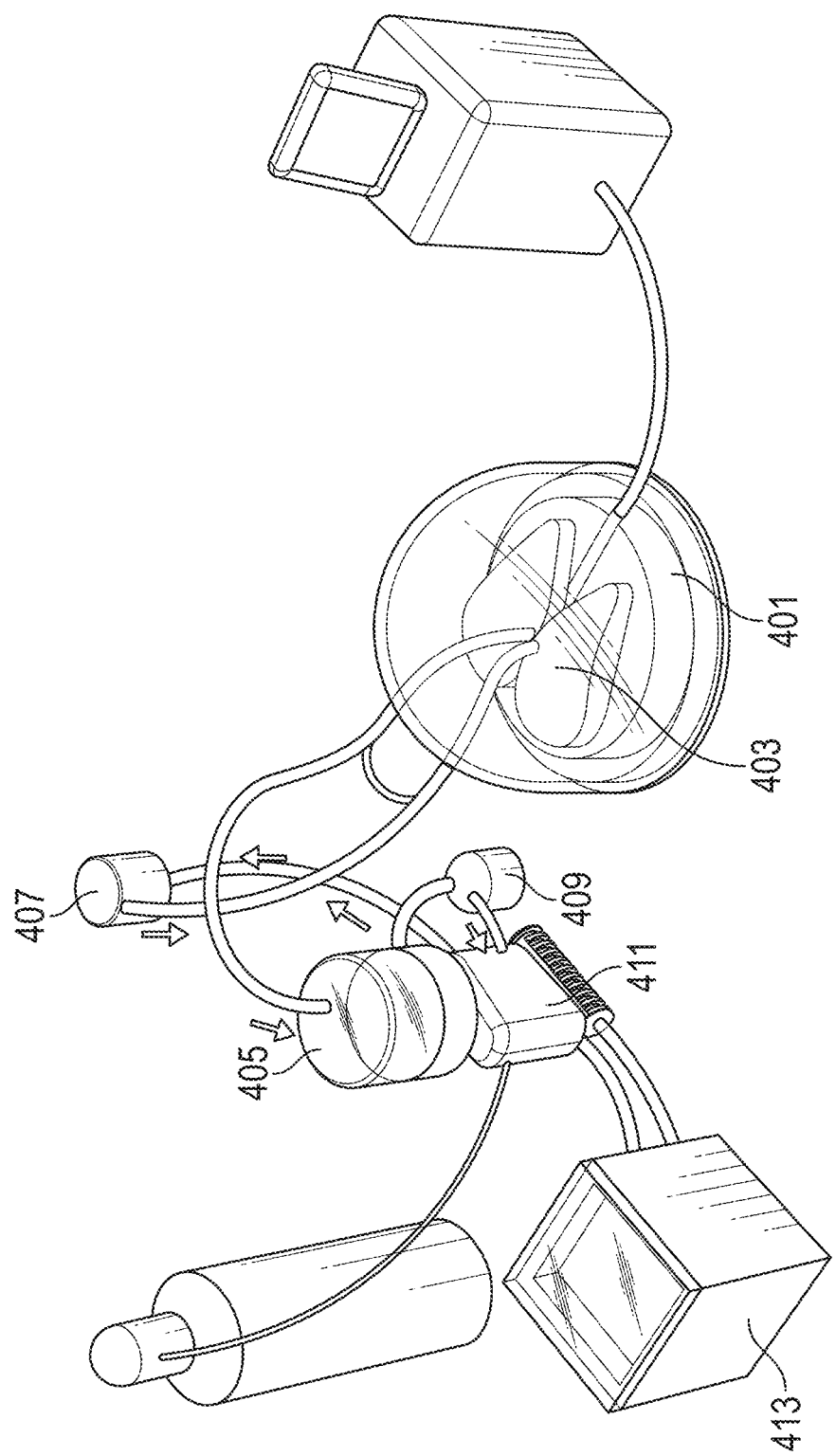
FIG. 4 is a schematic of an EVLP system.

A schematic of an EVLP system is shown in FIG. 4. An XVIVO™ chamber is shown at 401. Lungs 403 are placed within the XVIVO™ chamber 401. An ICU ventilator is connected to the XVIVO™ chamber to deliver breathes into the organ inside the XVIVO™ chamber (XVIVO® chamber available from Vitrolife AB, Sweden). A reservoir is shown at 405. The lung perfusate leaves the lungs and enters the reservoir 405. The lung perfusate may pass through the irradiation apparatus (not shown) after leaving the lungs. In one embodiment, the lung perfusate may pass through the irradiation apparatus after leaving the pump but before entering the oxygenator. In other embodiments, the lung perfusate may pass through the irradiation apparatus at other points in the EVLP circuit.

From there, the lung perfusate is pumped using a centrifugal pump 409 into the membrane (De)oxygenator 411 where it is deoxygenated by a gas mixture (for example 86% $N_2$, 8% $CO_2$ and 6% $O_2$) and warmed to normothermia and heat exchanger (heater/cooler) 413. The lung perfusate then optionally passes through a leukocyte filter 407 before reentering the lungs 403.

Referring to FIG. 16, there is shown a block diagram of an EVLP system 1600 including an irradiator. The EVLP system 1600 includes an irradiation system 1617, an organ chamber 1601, an ICU ventilator 1615, a reservoir 1605, a centrifugal pump 1609, a membrane (deoxigenator) 1611, a deoxygenation gas tank 1621, an heater/cooler exchanger 1613 and a leukocyte filter 1607. For example, the irradiator is part of the irradiation system. For example, irradiation system can also be used with an EVP system for irradiating a solution. For example, irradiation system can also be used with an EVKP system for irradiating a solution. For example, irradiation system can also be used with an EVCP system for irradiating a solution. For example, irradiation system can also be used with an EVHP system for irradiating a solution.

Referring back to FIG. 16, an outlet of the leukocyte filter 1607 is connected to an inlet of the irradiation system, such that the perfusion solution/perfusate flows 1631 from the leukocyte filter to the irradiation system. An outlet of the irradiation system is connected to an inlet of organ chamber 1601, such that irradiated perfusion solution/perfusate flows 1632 from the irradiation system to the organ chamber at 1601. There is a bridge clamp 1623 between the organ chamber-lung connection and the organ chamber-reservoir connection. When activated, the bridge clamp allows the perfusation solution to flow from the irradiation system 1617 to the reservoir 1605 without passing through the organ chamber.

For example, the irradiation system 1617 can be the apparatus described in FIGS. 1A and 1B and FIG. 2. For example, the irradiation system 1617 can be the system described in FIGS. 17 and 19A-D.

For example, the organ chamber can be an XVIVO™ chamber. For example, an organ (such as lungs) 1603 can be placed within the XVIVO™ chamber 1601 for treatment.

For example, the irradiation system 1617 can be connected between the membrane (deoxigenator) and the leukocyte filter. For example, the irradiation system can be connected between the centrifugal pump and the membrane (deoxigenator). For example, the irradiation system can be connected between the reservoir and the centrifugal pump. For example, the irradiation system can be connected between the organ chamber and the reservoir.

The person skilled in the art will recognize that other systems (such as an EVP, EVKP, EVCP and EVHP systems) may not have a respirator. In this case, the irradiation system, and in particular, the irradiator, can be placed anywhere in the main circuit of such systems, and preferably prior to entry into the organ chamber.

Also provided are methods for de-contaminating donor organs of potentially infective microorganisms. Examples of methods for inactivating microorganisms, including for example, virus such as one or more of HCV virus, HIV, Hepatitis B, CMV, EBV, and adenovirus or bacteria such as one or more of a staphylococcal bacteria, e.g. *Staphylococcus aureus*, *Stenotrophomonas maltophilia*, and a pseudomonad bacteria e.g. *Psuedomonas aeruginosa* in a donor organ are described herein.

Accordingly as aspect of the invention is a method inactivating microorganisms, including viruses and bacteria, in a donor organ, the method comprising:
  performing ex vivo perfusion (EVP) on the donor organ using a perfusion solution to produce a perfusate; and
  irradiating the perfusate.

In one embodiment, the solution (e.g. perfusate) may be treated with UVC light irradiation. In another embodiment, the perfusion solution may comprise a photoactivator such as methylene blue and be irradiated with red light.

The method can be to inactivate microorganisms, such as viruses including for example one or more of HCV virus, HIV, Hepatitis B virus, CMV, EBV, and adenovirus and/or bacteria such as one or more of staphylococcal bacteria, e.g. *Staphylococcus aureus; Stenotrophomonas maltophilia*, and pseudomonad bacteria, e.g. *Psuedomonas aeruginosa*.

In an embodiment, the method comprises performing EVP on the donor organ performed for at least or about 2 hours, at least or about 4 hours, at least or about 6 hours, at least or about 8 hours or at least or about 9 hours, at least or about 12 hours optionally up to or about 18 hours.

UVC light irradiation and/or PDT may efficiently inactivate the microorganisms within 1 hour or within 2 hours. Accordingly, the perfusate may be irradiated for at least 1 hour, at least or about 2 hours, at least or about 3 hours, at least or about 4 hours, at least or about 5 hours, at least or about 6 hours, up to or about 7 hours, up to or about 8 hours, up to or about 9 ours, at least 10 hours, at least 11 hours or at least 12 hours or more. For example, the irradiation can be performed for at least two and up to 18 hours, optionally up to 15 hours, up to 12 hours, up to 9 hours, up to 6 hours or up to 4 hours, optionally for a same period as the EVP.

The irradiation is optionally performed for a portion of the EVP or during the entire time of the EVP.

In some embodiments, the methods use one or more of the apparatuses, systems or devices described herein.

In an embodiment, the method is for decontaminating an organ for transplantation, wherein the method comprises
  perfusing the infected organ with a perfusion solution by EVP to provide a perfusate;
  irradiating the perfusate with a light therapy selected from UVC or PDT for at least 2 hours; thereby providing a decontaminated organ.

In one embodiment, the irradiation is UVC

In another embodiment, the perfusion solution comprises a photosensitizer. The photosensitizer can be methylene blue. In embodiments using methylene blue, the irradiation is red light. Other examples include the photosensitizer, benzoporphyrin derivative monoacid ring A (BPD-MA) which is virucidal towards enveloped viruses when activated by light.

In some embodiments, the EVP circuit comprises an irradiator that provides the irradiation. In other embodiments, the irradiator is an irradiator described herein in FIGS. 1A, 1B, 2, 17 and 19A-D or comprising a component described herein such as the UV lamp specifications or receptacle.

In one embodiment, the organ is selected from a lung, kidney, heart and liver.

In one embodiment, the EVP is standard EVP. In an embodiment, the EVP is EVLP.

Standard EVLP involves pumping a nutrient solution such as Steen Solution™ through the blood vessels of the lungs while at the same time supplying them with oxygen from a ventilator machine.

In an embodiment, the perfusion solution is Steen Solution.

In an embodiment, the perfusion solution comprises an oxygen carrier.

In one embodiment, a method for decreasing and/or inactivating microorganisms, in a donor organ includes: performing standard EVP with or without irradiation; changing the perfusate; and performing EVP again with irradiation. In one embodiment, the perfusate or a portion thereof may be changed every hour. In one embodiment, the perfusate may be changed every 2 hours. In one embodiment, the perfusate may be changed every 3, 4, 5 or 6 hours. In an embodiment, this method includes: performing EVP for at least three hours with or without irradiation; changing the perfusate or a portion thereof with fresh perfusion solution; and performing EVP with irradiation, for example for six hours.

In an embodiment, the method comprises performing EVP, with or without irradiation; changing the perfusate or a portion thereof; and performing EVP for one or more subsequent periods with irradiation for at least one of the subsequent periods.

In an embodiment, the EVP is EVLP. In another embodiment, the EVP is EKP. In yet another embodiment, the EVP is EVCP. In yet another embodiment, the EVP is EVHP.

The methods described herein can be used with any organs, whether or not known to be infected with a virus or bacteria. Using light therapy as described here, can prevent contamination or prevent transmission of an infection not routinely screened for prior to transplantation or not detected.

The methods described herein may in particular permit rescue of organs that are for example HCV positive. Accordingly a further aspect includes a method for rescuing donor organs obtained from an individuals suffering from an infection, for use in transplantation into a recipient, where said infection would have disqualified said organ for use in transplantation, said method comprised of: perfusing said organ with a perfusion solution in an ex-vivo system for a first period of time, where said period of time is determined on the basis that the individual was not infected to produce a perfusate; and irradiating said perfusate for a second period of time, applied concurrently with the perfusion of said organ, wherein said second period of time being no greater than 9 hours.

In an embodiment, the perfusate is irradiated for at least 2 hours or for a time period described herein. The parameters such as the flow rate etc can be for example a parameter described herein.

In some embodiments, the method further comprises transplanting the organ.

In yet other embodiments, after irradiating the perfusate, the perfusate can optionally assessed for infectivity prior to or after transplant.

Accordingly also provided is a method of transplanting an infected organ, the method comprising
    perfusing the infected organ with a perfusion solution by ex vivo perfusion (EVP) to provide a perfusate;
    irradiating the perfusate with a light therapy selected from UVC or PDT for at least 2 hours; transplanting the perfused and light therapy treated organ into a subject.

The perfusion and irradiation with UVC or light comprising red light can be according to any of the parameters described herein.

As mentioned, where PDT is used, the perfusion solution comprises a photoactivator such as methylene blue.

In one embodiment, a method for decreasing microorganisms, optionally virus such as one or more of HCV virus, HIV, Hepatitis B, CMV, EBV, and adenovirus or bacteria in a donor lung comprises: performing UVC irradiation on a lung perfusate during standard EVLP, preferably, performing UVC irradiation on the lung perfusate for at least 2 hours, optionally 2 to 12 hours during EVLP. UVC irradiation involves passing the lung perfusate into the apparatus for irradiating the lung perfusate as described above. As shown in the Examples, UVC irradiation does not affect the albumin in Steen Solution™.

The following non-limiting examples are illustrative of the present disclosure:

Example 1

Effect of EVLP in Altering Tissue and Lung Perfusate Levels of HCV

Methods

HCV+ human lungs declined for lung transplant were assessed. The retrieval and flush techniques used are similar to clinical practice. Double lung blocks were split and placed in two separate EVLP circuits and compared. Viral titers were measured by qtPCR.
    Group 1: control n=3 received standard EVLP for 9 h (control)
    Group 2: circuit/perfusate exchange n=3. Circuit and perfusion exchange was at 3 hours.

Results

Figure 5:
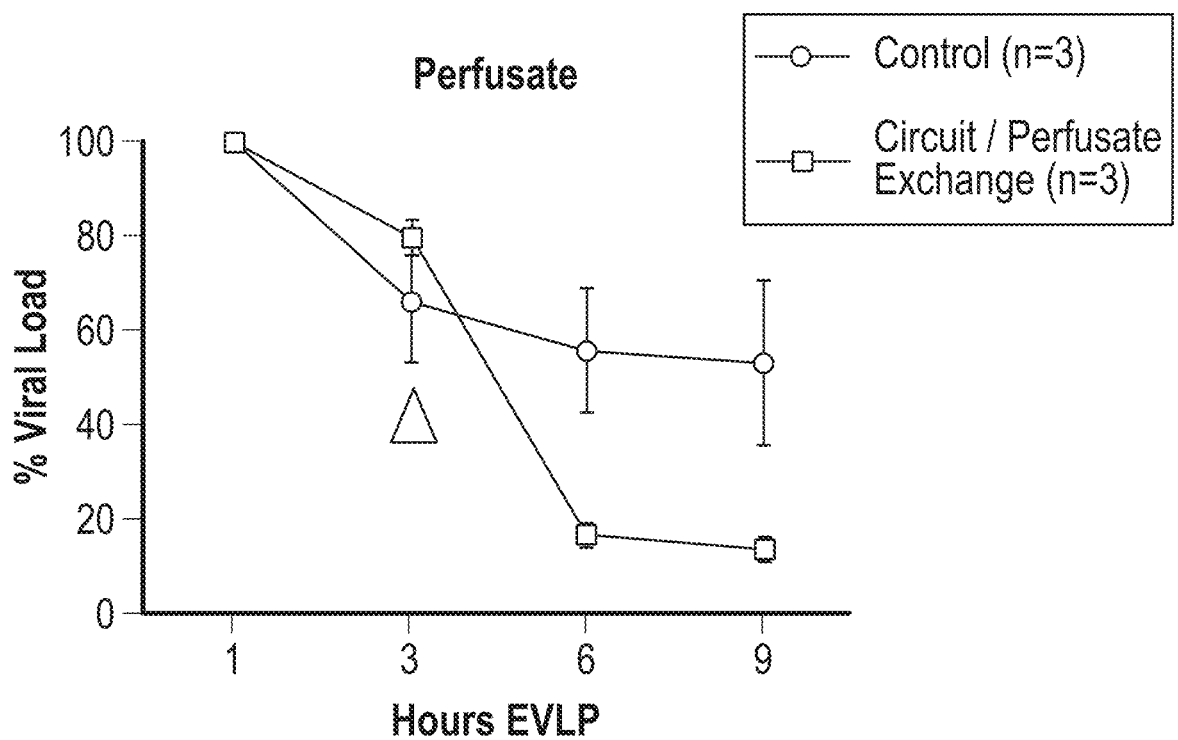
FIG. 5 is a set of graphs showing changes in % viral load in lung perfusate and lung tissue after various treatments.
Figure 5:
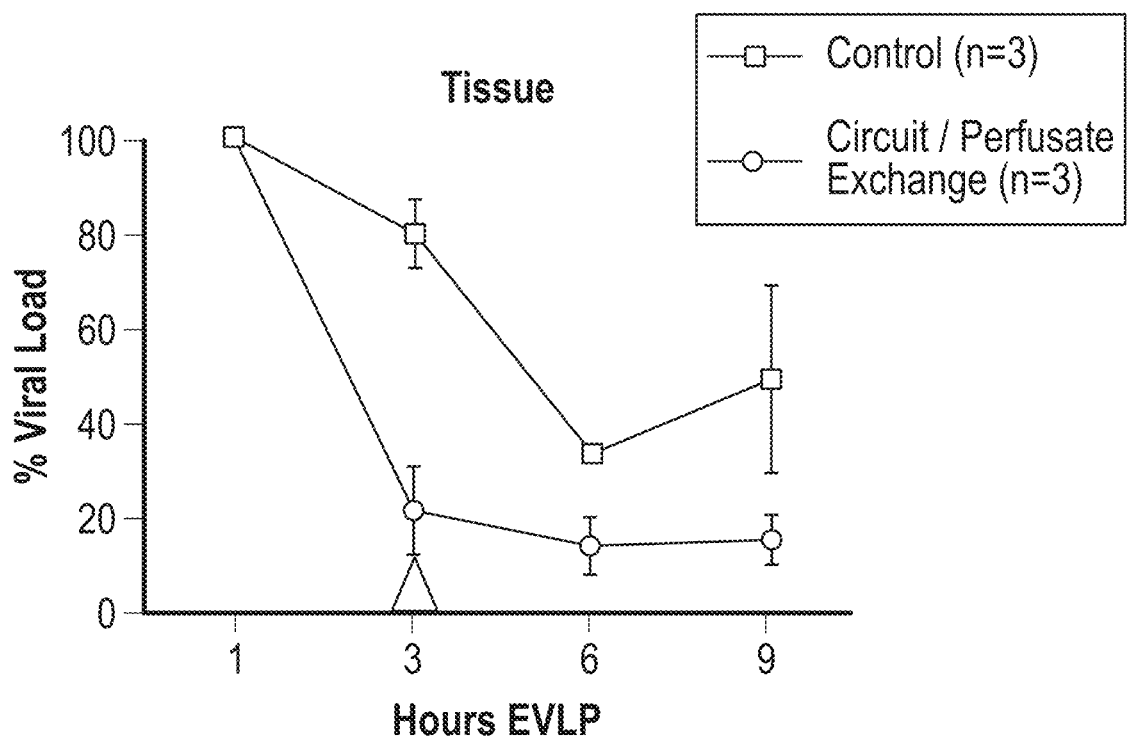

FIG. 5 demonstrates the decrease in viral load seen.
Table 1 shows that viral load was undetectable in lungs from donors with low viremia.

| | 1 | 2 | 3 | 4 | 5 | 6 | 7 | 8 |
|---|---|---|---|---|---|---|---|---|
| Donor Viral Load | N/A | 1238616 | 94 | 1140685 | 997686 | 29957 | 128 | 554297 |
| Perfusate Viral Load Baseline | 15004 | 2554 | 0 | 790 | 2165 | 119 | 12 | 1480 |

-continued

|  | 1 | 2 | 3 | 4 | 5 | 6 | 7 | 8 |
|---|---|---|---|---|---|---|---|---|
| Perfusate Viral Load 3 h | 11480 | 1763 | 0 | 596 | 1676 | 157 | 0 | 1410 |
| Perfusate Viral Load 6 h | 2036 | 1569 | 0 | 441 | 1630 | 195 | 0 | 839 |
| Perfusate Viral Load 9 h | 1954 | 1579 | 0 | 145 | 1664 | 266 | 0 | 486 |
| Tissue Viral Load Baseline | 4044 | 9060 | 0 | 634 | 460 | 223 | 0 | 1254 |
| Tissue Viral Load 3 h | N/A | N/A | 0 | N/A | N/A | N/A | 0 | N/A |
| Tissue Viral Load 6 h | 1415 | 3674 | 0 | 67 | 157 | 36 | 0 | 119 |
| Tissue Viral Load 9 h | 3640 | 3790 | 0 | 55 | 83 | 61 | 0 | 41 |

Example 2

Device for Application of Light Based Therapies (UVC and PDT) for Use During EVLP UVC light irradiation (253.7 nm; 450 microW/cm2) can be used to inactivate HCV in cell culture (e.g. within 60 s and within 2 min in human serum).

A customized irradiation apparatus was designed and tested as shown in FIGS. 1 and 2.

Example 3

Effect of UVC on Lung Perfusate HCV Quantities and Infectivity

Methods

Perfusate radiation: UVC: 253.7 nm; 450 microW/cm2

HCV+ human lungs declined for lung transplant were assessed. The retrieval and flush techniques used are similar to clinical practice. Double lung blocks were split and placed in two separate EVLP circuits and compared (Group 1 and 2). Viral titers were measured by qtPCR.

Group 1: control n=3 received standard EVLP for 9 h

Group 2: UVC n=3; UVC irradiation 9 h

Group 3: circuit/perfusate exchange (Wash) n=3. Standard EVLP 3 h/Change circuit/perfusate/standard EVLP 6 h

Results

Results are shown in FIG. 6

Example 4

Mini-EVLP Circuit and Irradiator

A mini EVLP and irradiator was constructed as shown in FIG. 7. It is suitable for assessment of different light wavelengths/fluence (e.g. a stream of particles crossing a unit area). It was used to assess the effect on perfusion solution degradation after UVC exposure. The UVC bulb lamp used was 0.9 J/s; 253.7 nm and/or 4 W/29V/0.17 A, with a diameter of 16 mm, length of 136 mm and providing a fluence of 31 $mW/cm^2$. In this model, the irradiator comprises a quartz tube that houses the UV bulb and a regular glass which forms a chamber for receiving the solution, optionally having a tube length of 133 mm and a wall thickness of up to 21.6 mm The priming volume was 150 mL. A solution is pumped into the irradiator. The solution may be lung perfusate. A centrifugal pump is pumping the solution into the irradiator at a controlled flow rate. The controlled flow rate may be between 0.1 to 2 liters per minutes. The solution output the irradiator and is fed to a reservoir. An external heater may provide heat to the solution inside the reservoir. The solution inside the reservoir may be fed again to the irradiator by the centrifugal pump. A stopcock may collect samples from the reservoir.

Method and Results

Fresh Steen solution (150 mL) irradiated on the mini EVLP was compared to non-irradiated Steen perfusion solution. The solution was treated for 180 minutes and double validated. As shown in FIG. 8, there was no effect on serum albumin.

UCV was able to eliminate HCV in the EVLP minicircuit. Fresh Steen solution (150 mL) was transfected with HCV serum (from HCV+ lung donors). The initial viral load was 6000 UI/mL on average. Perfusate irradiation was conducted for 3 hours (UIVC-0.9 J/s). Results are shown in FIG. 9. As indicated by the inverted triangle, in 2 out of 3 cases, after 120 minutes of UVC exposure, a non-detectable viral load was achieved.

In the Examples it is demonstrated that standard EVLP decreases microorganisms, preferably virus such as one or more of HCV virus, HIV, Hepatitis B, Cytomegalovirus (CMV), Epstein-Barr virus, (EBV), and adenovirus in a donor lung and this effect is enhanced by circuit perfusate exchange, for example at 3 h. UVC was effective at inactivating HCV.

Example 5

Infectivity Assay

JFH-1 HCV strain is used to transfect Huh 7.51 hepatocytes as shown in FIG. 10. Transfect Steen solution with manufactured HVS for purposes of use in the mini EVLP system can be made and used for example to determine suitable or optimal conditions for inactivating microorganisms, preferably virus such as one or more of HCV virus, HIV, Hepatitis B, Cytomegalovirus (CMV), Epstein-Barr virus, (EBV), and adenovirus.

Example 6

Methods

Rejected lungs from 8 HCV+ donors were used for the study. Double lung blocks were separated and placed in 2 independent EVLP circuits for 9 hours. One lung was used as the control lung (standard EVLP protocol), whereas the other lung was subjected to different treatment conditions: 1: Intense lung wash (replacement of perfusate solution and circuit after 3 h of EVLP); 2: Ultra Violet C (UVC) light applied to circuit using a specifically design device. The effect of UVC light into virus load was also evaluated in specifically designed EVLP mini-circuit (circuit without the lungs) using different virus quantities. Virus load was measured at different time points in lung and perfusate using Abbott RealTime HCV assay.

Results

Figure 6:
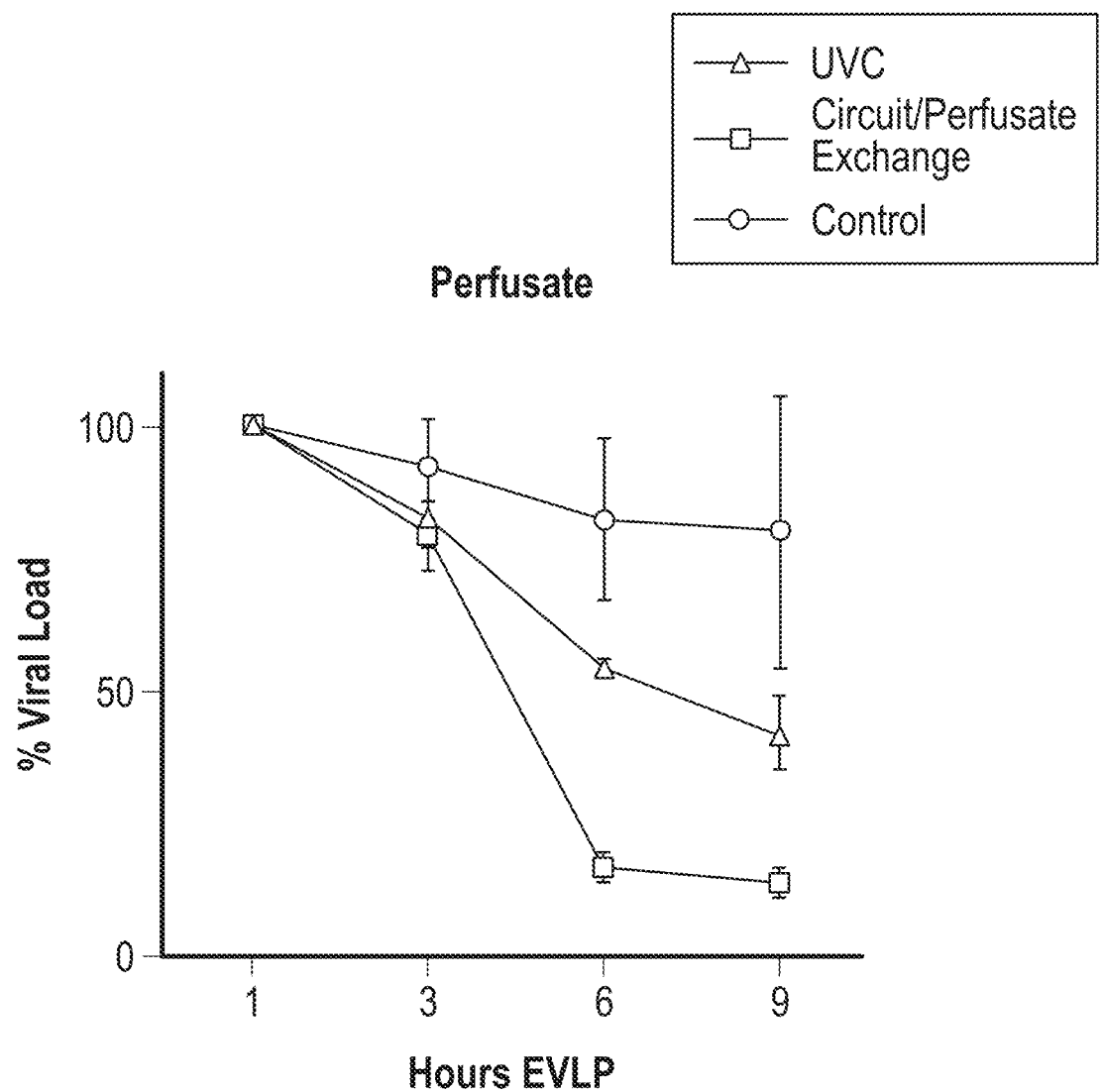
FIG. 6 is a graph showing % viral load in lung perfusate after various treatments.
Figure 9:
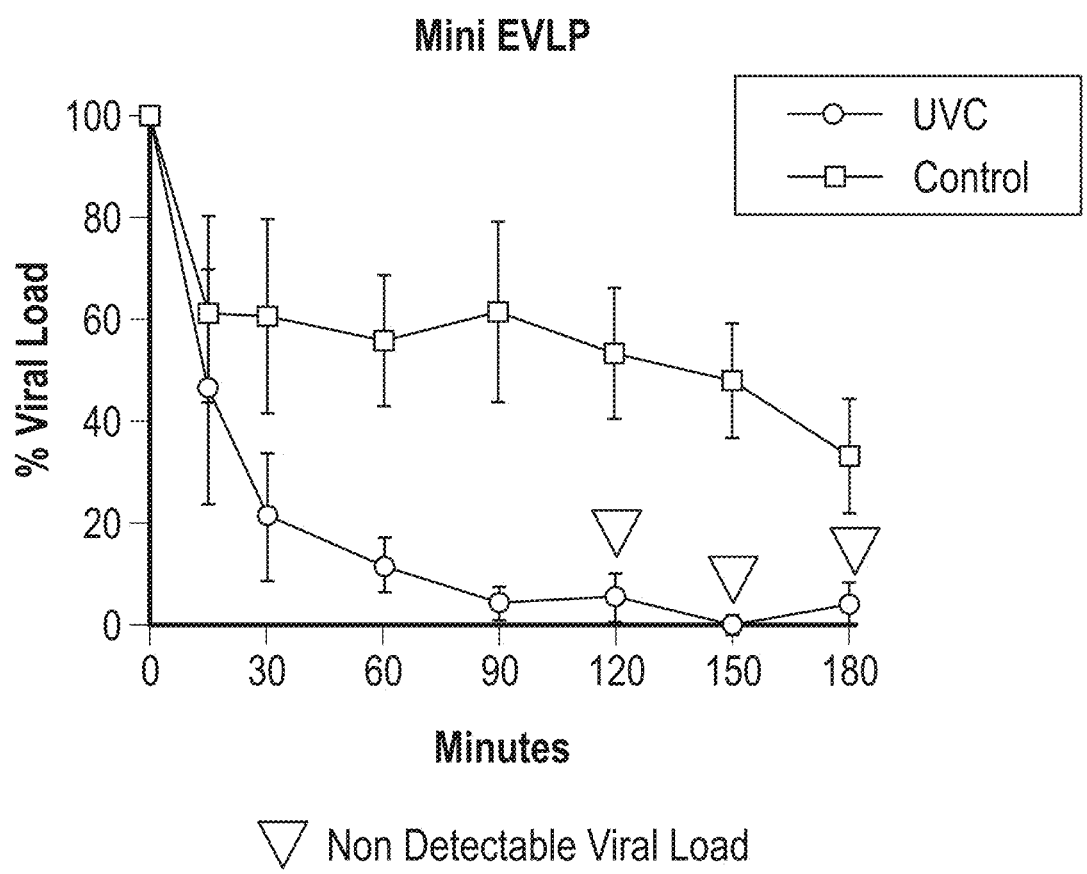
FIG. 9 is a graph showing % viral load after Mini EVLP and UVC exposure.
Figure 10:
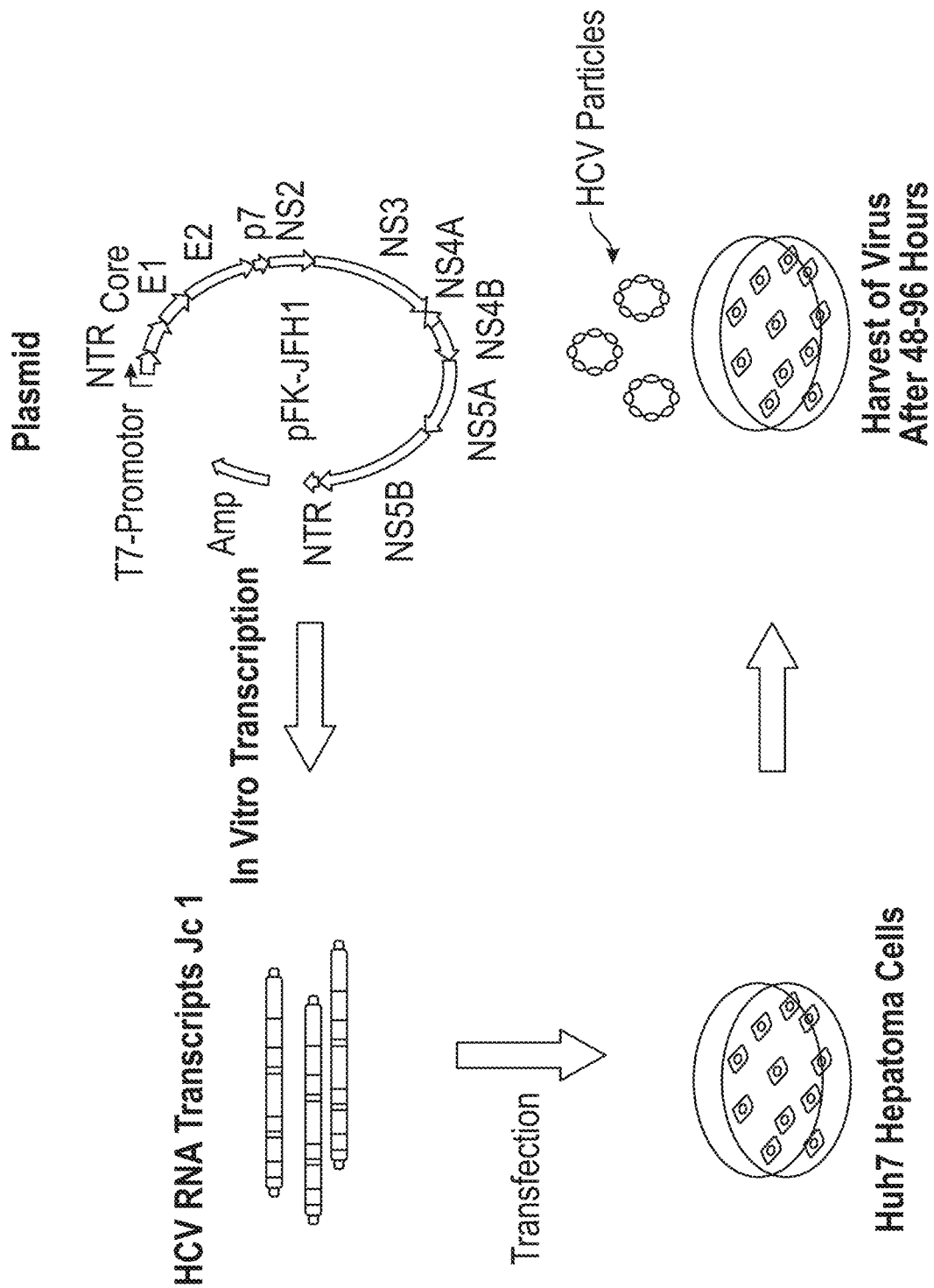
FIG. 10 is a schematic illustrating an infectivity assay.

In 2 out of 8 donors, no HCV virus was detected in the lungs during EVLP, and this was associated with low donor viremia. For the remaining 6 donors, lung wash was the most effective treatment to decrease HCV titres: 85.8% (±2.83; n=3) in the wash group vs. 57.6% (±6.78; n=2) in UVC group vs. 19.78% (±25.73; n=0.07) in control group (FIG. 6). UVC irradiation was very effective in the mini EVLP circuit at different HCV doses. After 180 minutes of UVC irradiation on the EVLP, the viral load decreased 95.7% (±4.3; n=3) from the initial load (FIG. 9). In two cases, an undetectable viral load was reached.

EVLP can be a platform to significantly decrease microorganisms, preferably virus such as one or more of HCV virus, HIV, Hepatitis B, Cytomegalovirus (CMV), Epstein-Barr virus, (EBV), and adenovirus from a donor lung. Whether this approach would lead to decrease risk of transmission is unknown. Adjunct treatment strategies such as UVC may yield complete elimination of in a donor lung.

Example 6

Infectivity of Perfusate was Assessed in a Hepatocyte Cell Model

Figure 11A:
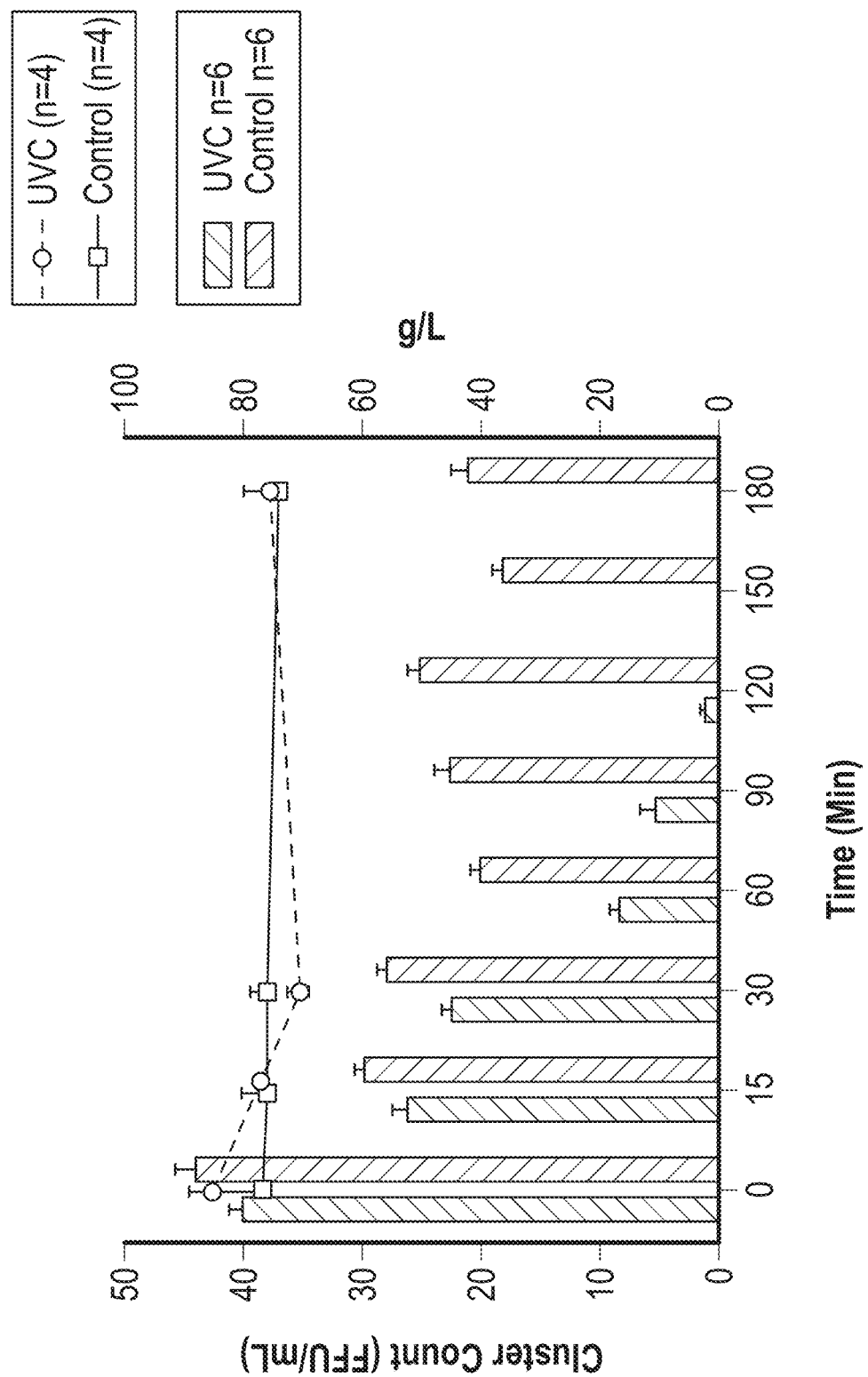
FIG. 11A is a graph showing infectivity and albumin levels in perfusate treated with UVC irradiation.

Ultraviolet-C irradiation was assessed as a suitable technology to inactivate Hepatitis C viruses in an infected organ perfusion solution, while keeping the human albumin from the solution still viable. The customized miniaturized perfusion system (mini-EVLP) and the irradiator shown in FIG. 7 and described in Example 4 was used. After being primed with an acellular organ perfusion solution as described in Example 4, a specific HCV (JFH-1, 1.5 $10^6$ copies/mL) surrogate was used to spike this solution. The system was tested for 180 min, 37° C. and 11/min. Two groups were tested (n=6, each): 1) Control, with no ultraviolet C irradiation, and 2) UVC, with 31 mW/cm$^2$ of light fluence. During the experiment, samples were taken at different timepoints, followed by transfection of the sample in a hepatocyte cell culture, (Huh 7.5.1), to test for the loss of infectivity. The effects of UVC on albumin (a key component of the organ perfusion solution) concentration and degradation was also tested. FIG. 11A (line graph) depicts that the albumin concentration was stable and no significant differences between two groups were detected. In the UVC group, no infectivity was found after 150 min of UVC irradiation, whereas the control group was still infectious (FIG. 11A, bar graph).

Figure 11B:
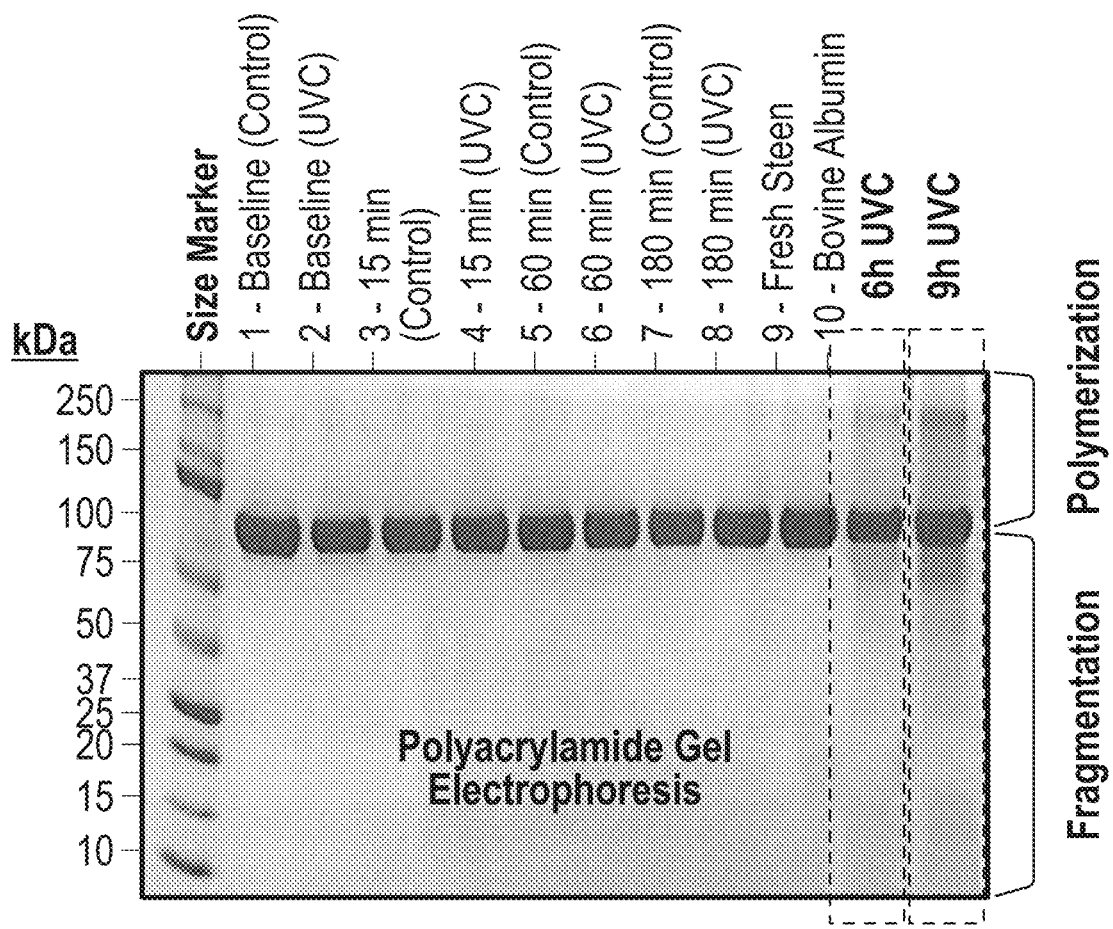
FIG. 11B is a blot showing levels of albumin in perfusate treated with UVC.

Even after 6 and 9 hours of UVC treatment, the albumin is largely intact as shown by polyacrylamide gel electrophoresis (FIG. 11B).

Example 7

Purpose: Lung transplant is a life-saving therapy for patients suffering from end-stage lung diseases. Ex vivo lung perfusion (EVLP) is being used for organ preservation and for lung infection treatment prior to transplantation. Ultraviolet-C light (UVC) irradiation is an effective virucidal and bactericidal treatment used for blood products prior to transfusion. In this study, the effects of UVC light irradiation and antibiotic therapy on common bacterial pathogens in a miniaturized EVLP model was investigated.

Figure 7:
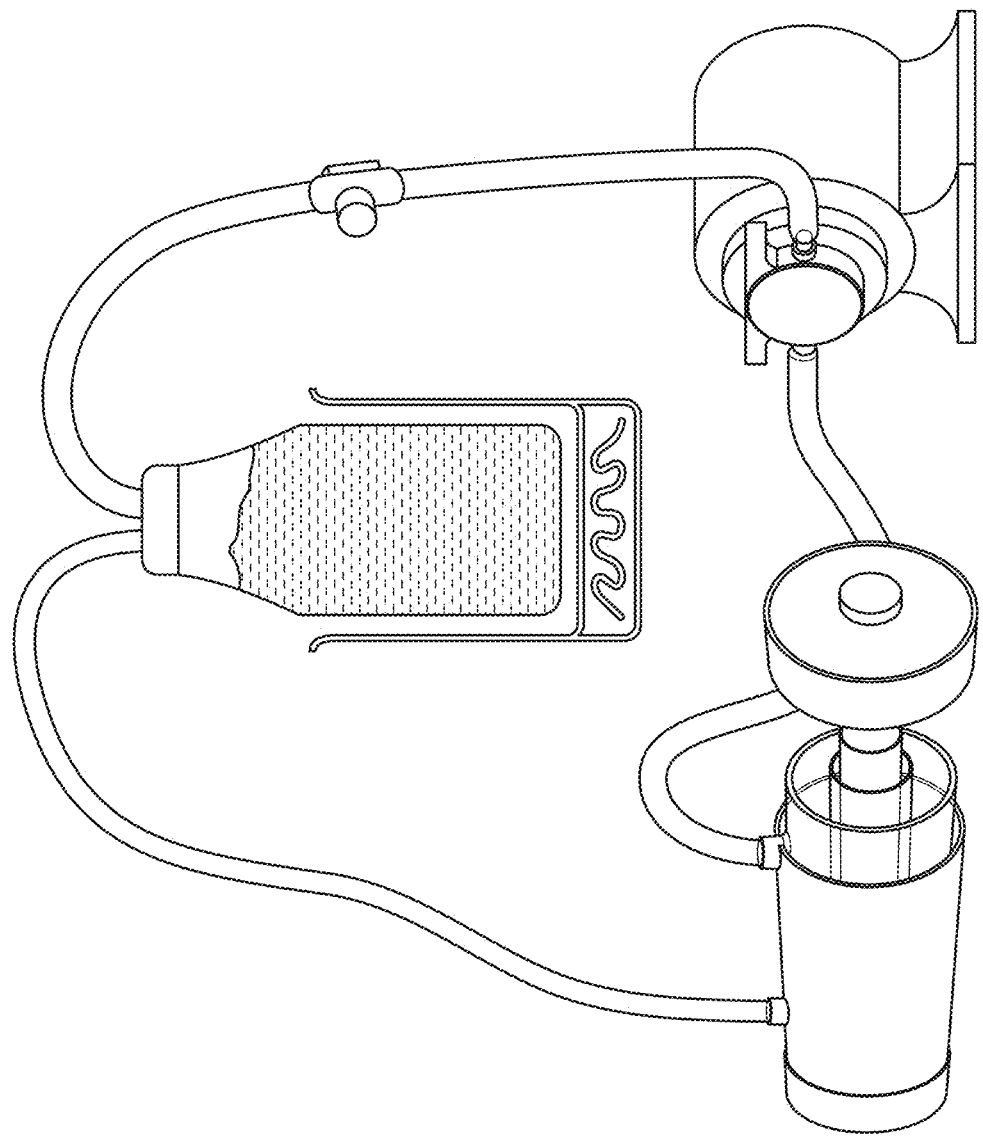
FIG. 7 is a schematic showing a mini-EVLP.
Figure 8:
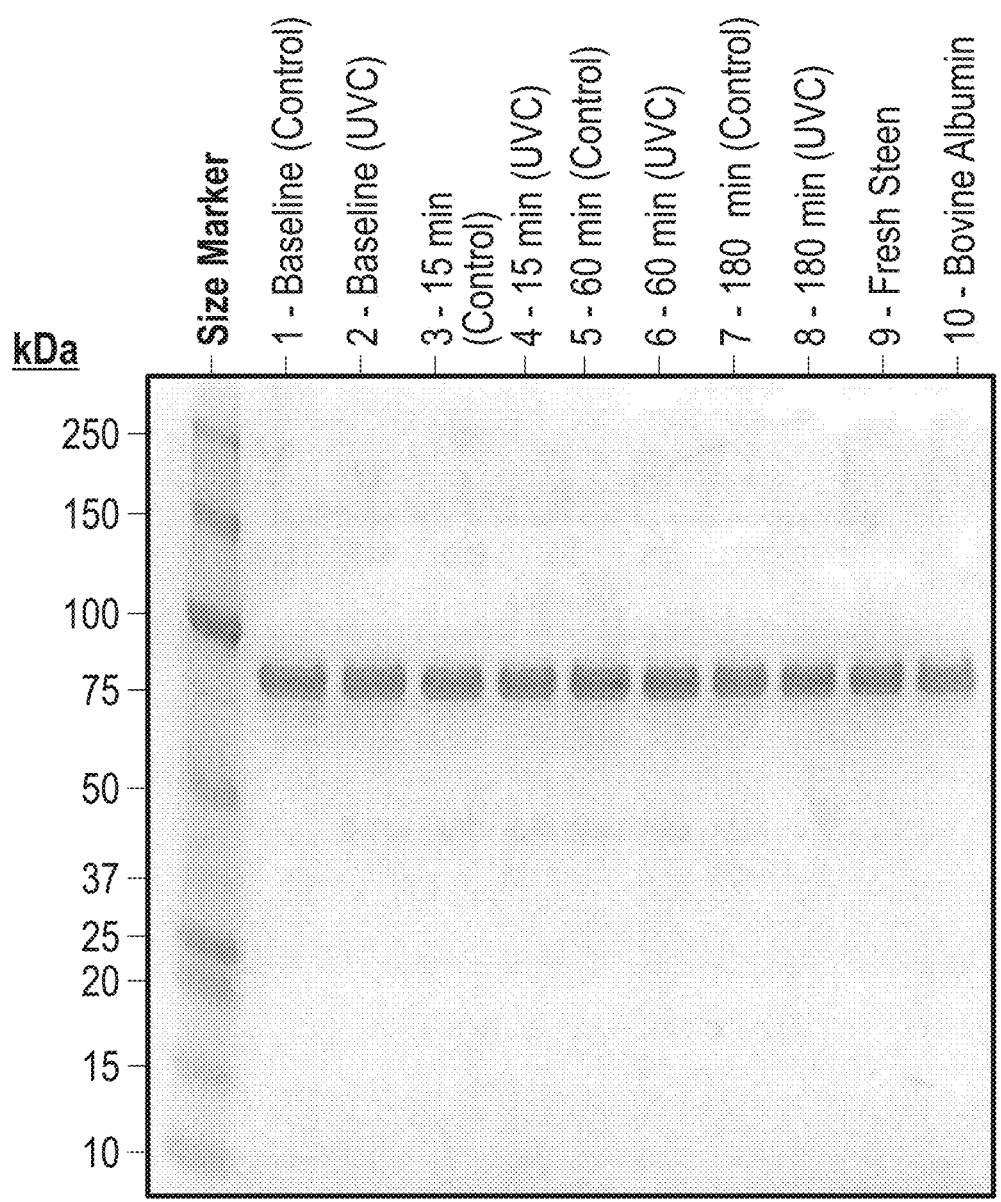
FIG. 8 is a polyacrylamide gel showing UVC does not affect albumin in Steen Solution.

Methods: A mixture of low-potassium-dextran lung perfusion solution and Lysogeny Broth (LB) media was spiked with $1.0 \times 10^5$ CFU/mL of *Staphylococcus aureus, Stenotrophomonas maltophilia*, and *Pseudomonas aeruginosa*. A mini EVLP and UVC irradiator was used (FIG. 7). After priming, the circuits were divided into three groups (n=4, each) and evaluated for 180 minutes: 1) Control (no treatment); 2) UVC (236 nm, 9 J/cm$^2$) and 3) Antibiotic (Imipenem/Cilastatin, 333 mg/L). Samples were taken at different timepoints and analysed, using LB Agar culture plates and bacterial DNA qPCR assay.

Results: Bacterial culture: No bacterial growth was seen after 15 minutes of UVC irradiation. In the antibiotic group, there were decreasing amounts of bacterial growth over time, however there was still bacterial growth after 180 minutes of treatment (0 vs. 15±2.3 colonies/plate, p=0.0476). In the control group, bacterial growth increased exponentially overtime. DNA qPCR analysis: UVC treatment was significantly more effective, causing 2 logs overall decrease vs. 1 log increase in control group (16S rRNA analysis) after 180 minutes. Moreover, UVC was the most effective after isolated analysis for each bacterial species (FIG. 12A-C).

Conclusion: UVC light applied in a modified normothermic ex vivo lung perfusion circuit effectively eliminated bacteria in the perfusate. This was significantly more effective than the addition of broad-spectrum antibiotics currently used in EVLP. UVC light could be an effective adjunct approach to maintain circuit sterility to protect from contamination or to eliminate bacteria shed into the perfusate from infected organs perfused ex vivo.

Example 8

Figure 13:
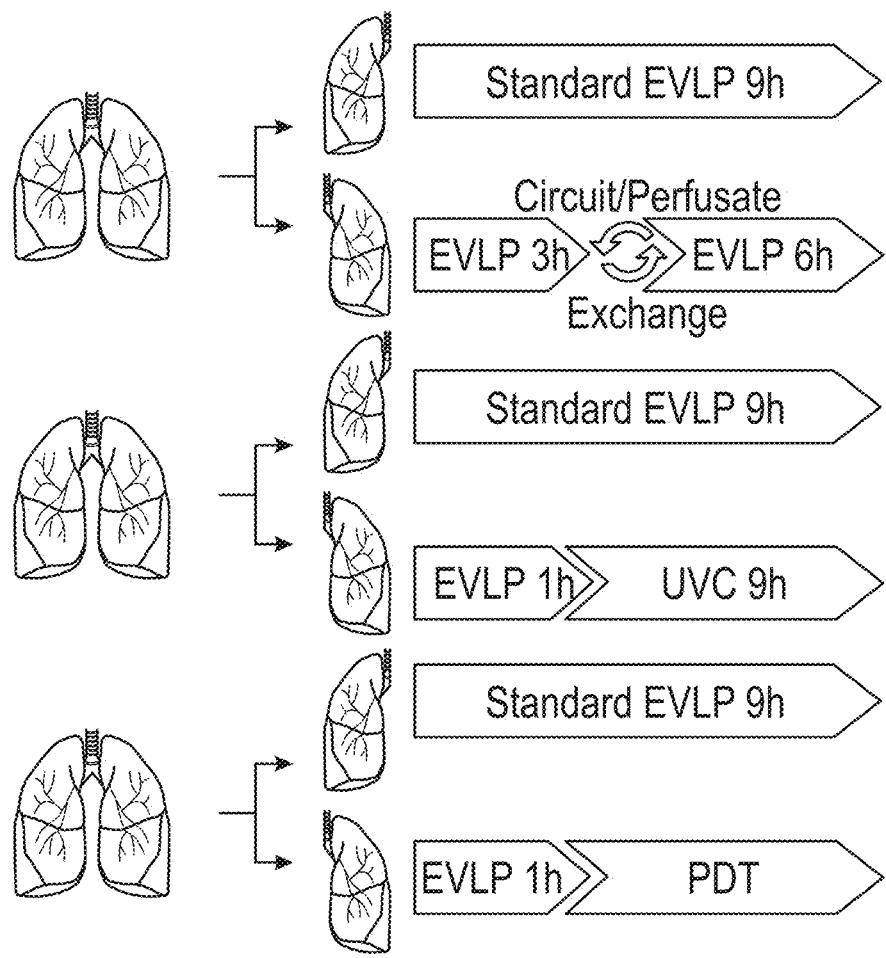
FIG. 13 is a schematic outlining the conditions tested.
Figure 14A:
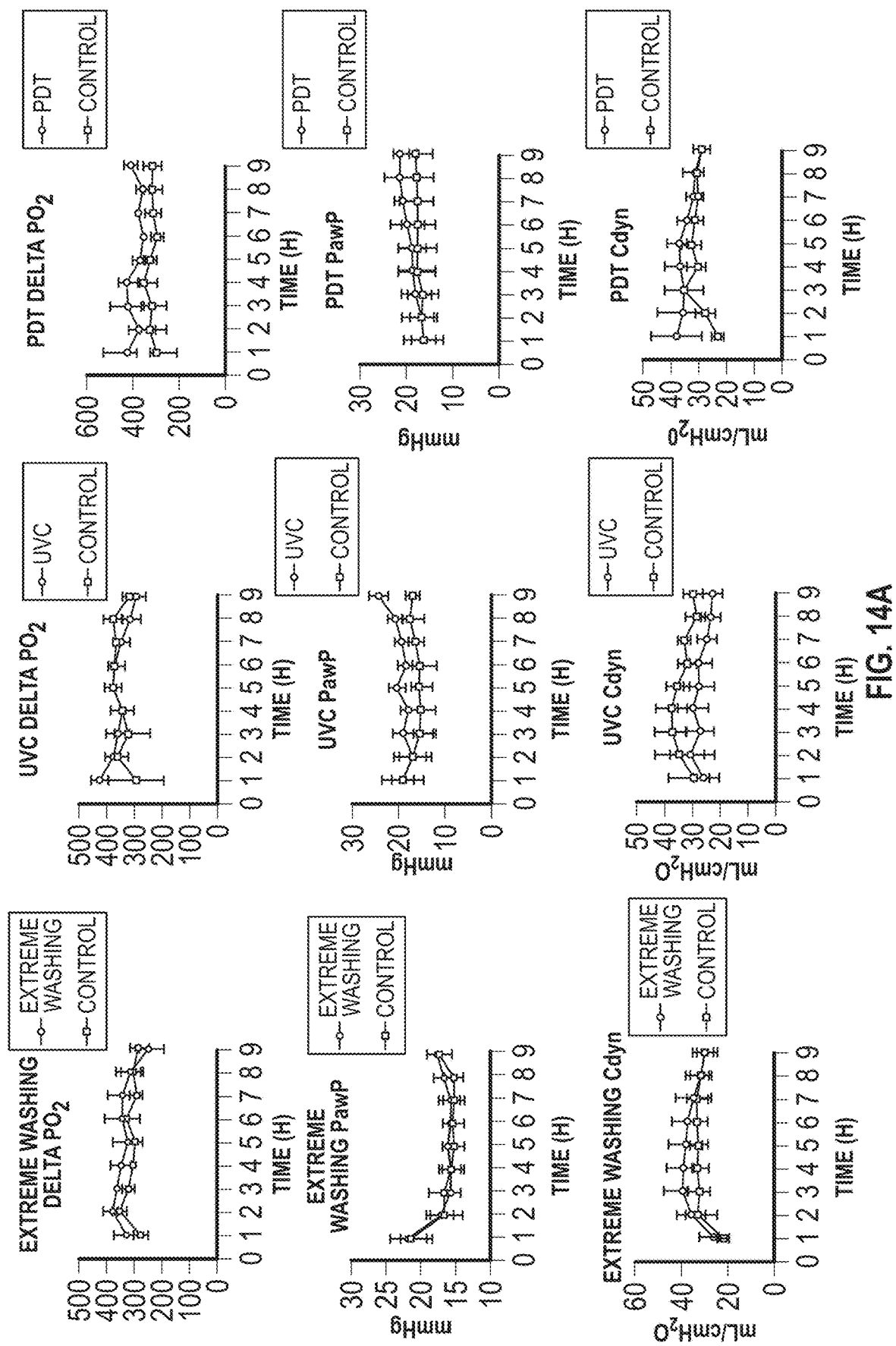
FIG. 14A is a series of graphs showing physiologic parameters during EVLP phase under conditions of extreme washing, UVC and PDT.
Figure 14B:
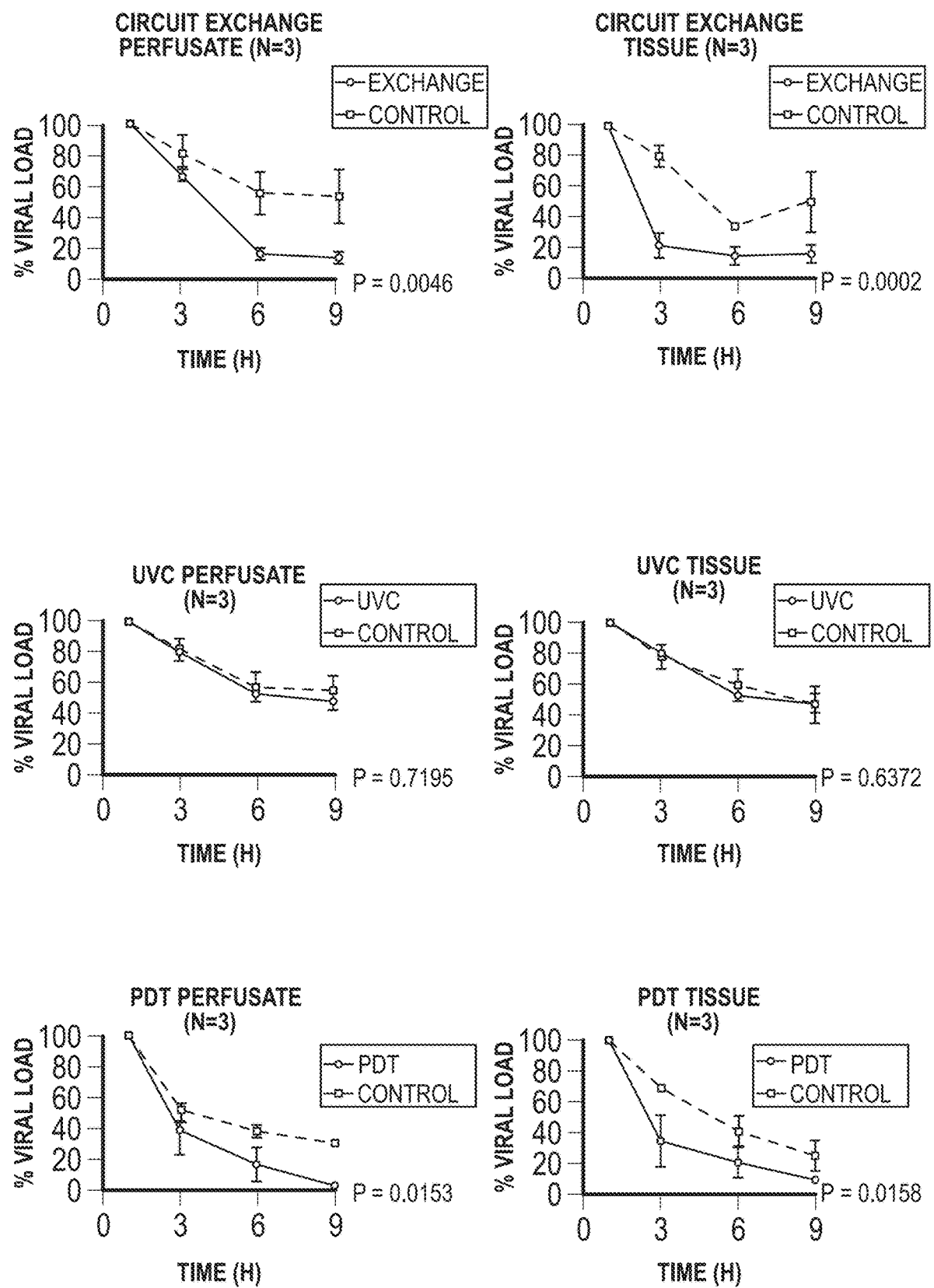
FIG. 14B is a series of graphs showing HCV viral load in perfusate of treated and control lungs.

Human Lung Studies: effect of EVLP and light therapies into HCV titers: In order to evaluate the effect of EVLP itself and also as a platform for light-based therapies against HCV titers in the lung tissue and perfusate solution, 9 rejected human lungs from NAT+ HCV donors. Donor lungs were recovered using standard protocols and flushed with cold Low-Potassium Dextran (LPD) solution and preserved at 4° C. as routine clinical practice. Following the pre-EVLP flush, the lungs were placed in 2 independent EVLP circuits for 9 hours. One lung was the control group (standard EVLP protocol, (n=9), whereas the other lung was randomly subjected to different treatment conditions (n=3, each) (FIG. 13A): (1) Intense lung wash (replacement of perfusate solution and circuit after 3 h of EVLP); (2) Ultra Violet C (UVC) light (260 nm, 4 W) applied to EVLP perfusate; (3) Photodynamic Therapy (PDT), using Methylene Blue (MB) diluted in the perfusion solution (1 umol/L) associated with red light irradiation (630 nm, 20 mW/cm$^2$). The advantage of such design is that both control and treated lungs come from the same donor (same virus load as baseline). Tissue biopsies were collected from lower, and upper lobes of the lungs at baseline and every 3 h during perfusion and perfusate samples were collected hourly. All samples were assessed for viral load quantification using RealTime PCR assay. The results were normalized for percentage of viral load decrease. To translate the application of light therapies to an EVLP system, a specific device suitable to be inserted inline in the EVLP circuit where different light wavelengths could be applied to treat the perfusion solution. The irradiator was introduced downstream of the leukocyte filter as shown in FIG. 16. Firstly, no significant difference was found in terms of ex vivo lung function during EVLP suggesting no immediate deleterious effect of UVC or PDT applied to the circuit (FIG. 14A). For example, no significant differences in delta P/F ratio, peak airway pressure and dynamic compliance were found when comparing control and study lungs in all the groups, during 9 hours of EVLP. Secondly, PDT ((Methylene blue 1 umol/L+630 nm/20 mW/cm$^2$) was the most effective treatment to decrease perfusate HCV titres (% reduction from baseline): 97.87% reduction (±0.71) vs. 69.49% (±0.89) in control group (p=0.0153), followed by intense lung wash: 85.8% reduction (±2.83) vs. 46.57% (±17.85) in control group (p=0.046) and UVC 57.6% reduction (±6.78) vs. 54.5% (±10.23) in control group (p=0.7195). PDT was also the most effective to decrease HCV titers in lung tissue: 90.96% reduction (±0.7028) vs. 75.46% (±8.2) in control group (p=0.0158), followed by intense lung wash: 84.1% reduction (±5.49) vs. 50.14 (±20.09) (p=0.0002) in control groups. The UVC group showed no significant difference when compared to control: 52% (±5.7) vs. 53.3% (±12.1) in control group (p=0.6372) (FIG. 14B).

Infectivity Assessments

Figure 15A:
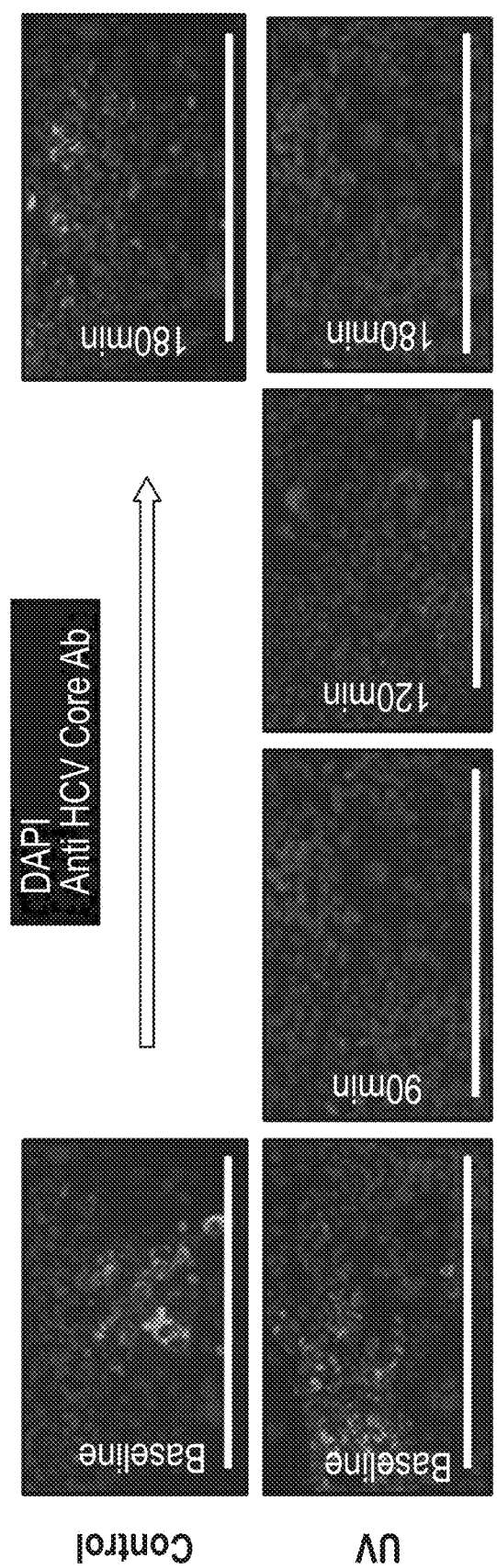
FIG. 15A is a series of images showing HCV virions stained using anti-HCV core antibody.
Figure 15B:
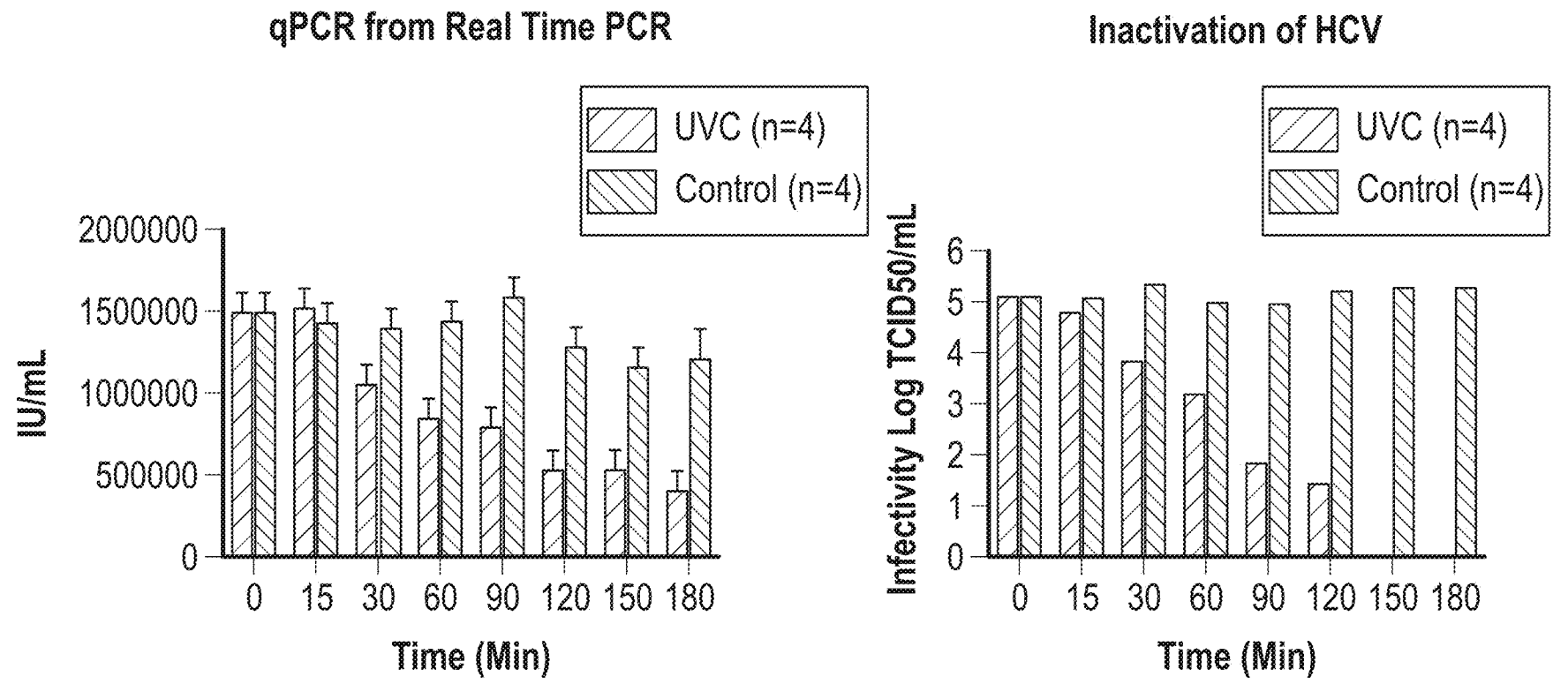
Figure 15C:
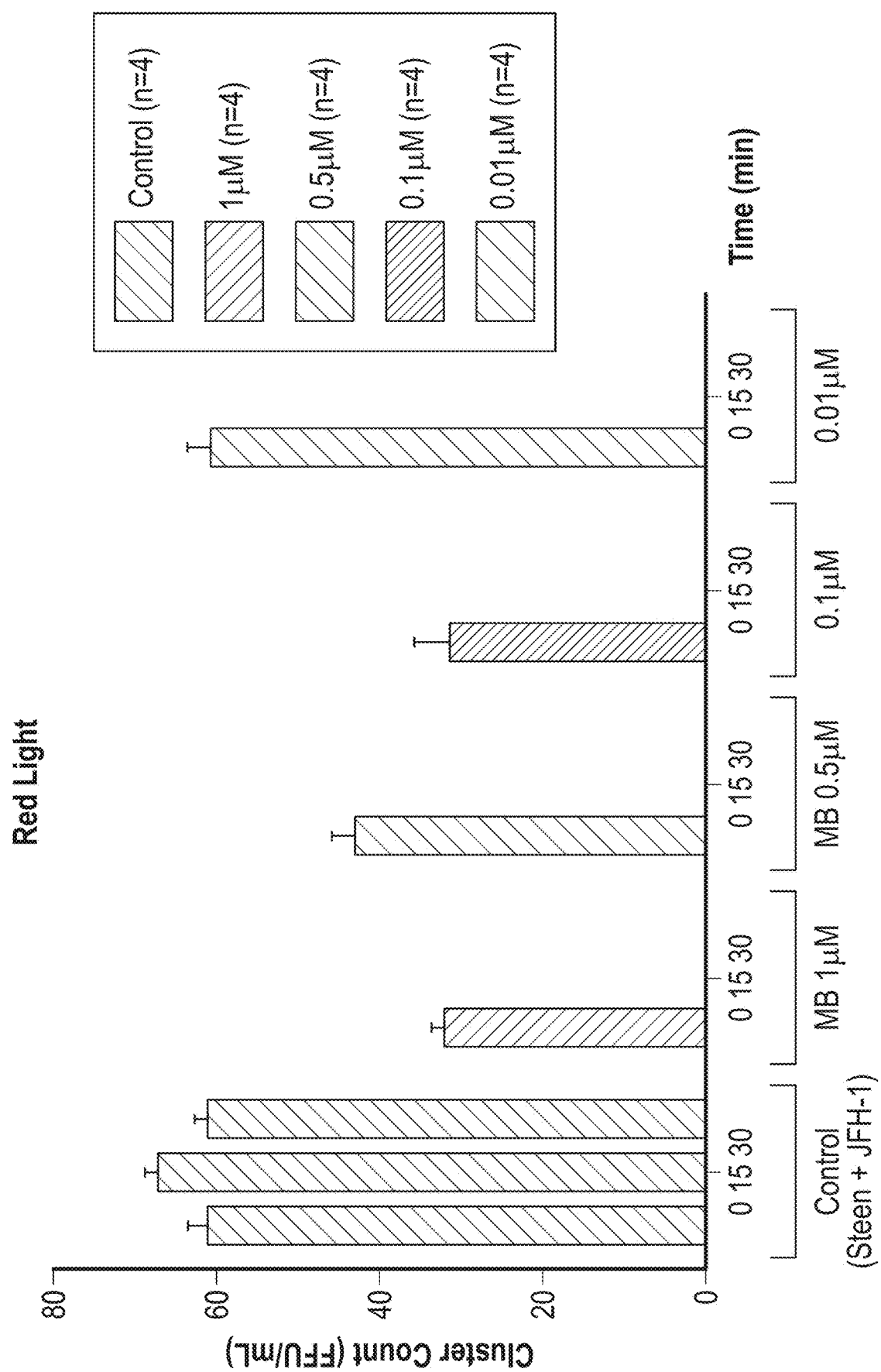
FIG. 15C is a graph showing effect of red light therapy on HCV infectivity.

One of the challenges related to the use of HCV qPCR as main efficacy endpoint is that PDT and UVC damages and/or fragments virions making them non-infectious, however they can still be detectable by qPCR. The qPCR targets the 5'UTR region of HCV RNA, which is the most conserved one after light-based therapies (Smith D B, Mellor J, Jarvis L M, et al. Variation of the hepatitis C virus 5' non-coding region: implications for secondary structure, virus detection and typing. *Journal of General Virology*. 1995; 76(7): 1749-1761. doi: 10.1099/0022-1317-76-7-1749). This effect highlights that our measurement of HCV RNA in the perfusate after EVLP is likely an underestimation of the antiviral effect of light therapy, as even detectable virus will have markedly diminished ability to infect naïve cells. Ideally, infectivity experiments would be replicated with virus from patients infected with HCV after light based treatments; however, HCV is very resistant to growth in in vitro systems. Thus, in order to evaluate the effect of light therapies during EVLP onto HCV infectivity loss, a HCV molecular clone (JFH-1, 2a HCV genotype) was used. This recently developed clone offered the opportunity to evaluate directly the HCV infectivity loss after different treatments using a Huh7-CD81 hepatocyte cell line, which is highly susceptible to HCVcc infection (Wakita T. Isolation of JFH-1 Strain and Development of an HCV Infection System. In: Hepatitis C. Methods in Molecular Biology™. Humana Press; 2009: 305-327. https://link-springer-corn.myaccess.library.utoronto.ca/protocol/10.1007/978-1-59745-394-3_23. Accessed Feb. 15, 2018). it was hypothesized that HCV virus albeit still detectable by qPCR in the perfusate solution would have no infection capability after treatment. To validate this principle, a specifically designed EVLP mini-circuit was used (FIG. 7) so that a known amount of JFH-1 virus could be added to circuit and exposed to light irradiation as used in the human lung experiments. After being primed with 250 mL of perfusate solution, the solution was infected with $1.5 \times 10^6$ copies/mL of HCV JFH-1 strain. After the perfusate was heated to 37° C., a 180-minute treatment was performed in three groups (n=4, each): (1) Control (no light irradiation), (2) UVC light (260 nm, 4 W) and, (3) PDT (MB diluted in different concentrations: 1 umol/L, 0.5 umol/L, 0.1 umol/L and 0.01 umol/L, in two different light conditions: 630 nm, 20 mW/cm$^2$ red light and regular room light). During the perfusion time in the mini-circuit, 1.5 mL aliquots were taken and used to spike a Huh 7.5.1 hepatocyte cell culture and kept for 72 h in DMEM supplemented with 10% FBS, under 37° C. plus 5% $CO_2$ setting. pH was controlled and a 30%-90% cell confluency was maintained. To illustrate infectivity, Huh 7.5.1 cells were stained with DAPI and HCV anti-core antibody, then hepatocytes clusters were counted (FIG. 15A). Samples were also analysed with RealTime PCR, for viral titration after treatment. The results are presented in cluster counts (FFU/mL). Herein, it is demonstrate that no infectivity was seen into Huh 7.5.1 cells after 150 min of UVC irradiation in the mini EVLP perfusate in all experiments, despite average qPCR viral count of 300,000 IU/mL after 180 min of irradiation (FIG. 15B). The PDT group demonstrated even further efficacy against HCV, and no infectivity was observed after 15 min of perfusion alone under red light exposure, and this effect was photosensitizer dose dependent (FIG. 15C). Importantly, red light treatment did not affect perfusate characteristics as assessed by albumin electrophoresis. Methylene blue was also activated with ambient light although its effect is weaker than with red light.

Taken together, these results demonstrate that 1: Regular EVLP protocol decreases HCV titers in human donor lungs by 40%; 2: Circuit and perfusate exchange after 3 H of EVLP decreases HCV titers in human donor lungs by 80% 3: PDT, using MB as a photosensitizer, decreases HCV titers in human donor lungs by 98%; 4: light-based therapies applied during EVLP are able to completely inactivate HCV, although virus fragments can still be detected by qPCR.

Pre-Clinical Safety Studies

Figure 15D:
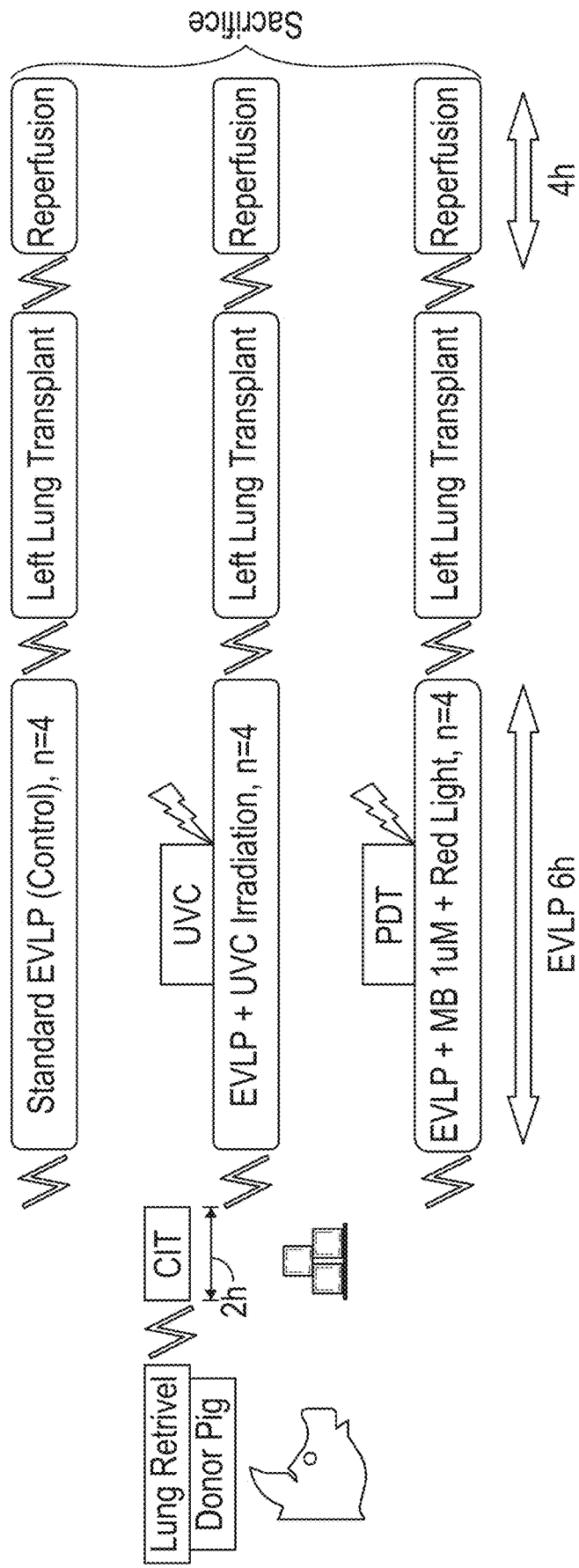
FIG. 15D is a schematic of a clinical trial.

In order to translate such approach to the clinical EVLP setting, the safety of applying UVC and PDT during EVLP was assessed using a pre-clinical large animal transplant model (FIG. 15D).

Figure 15E:
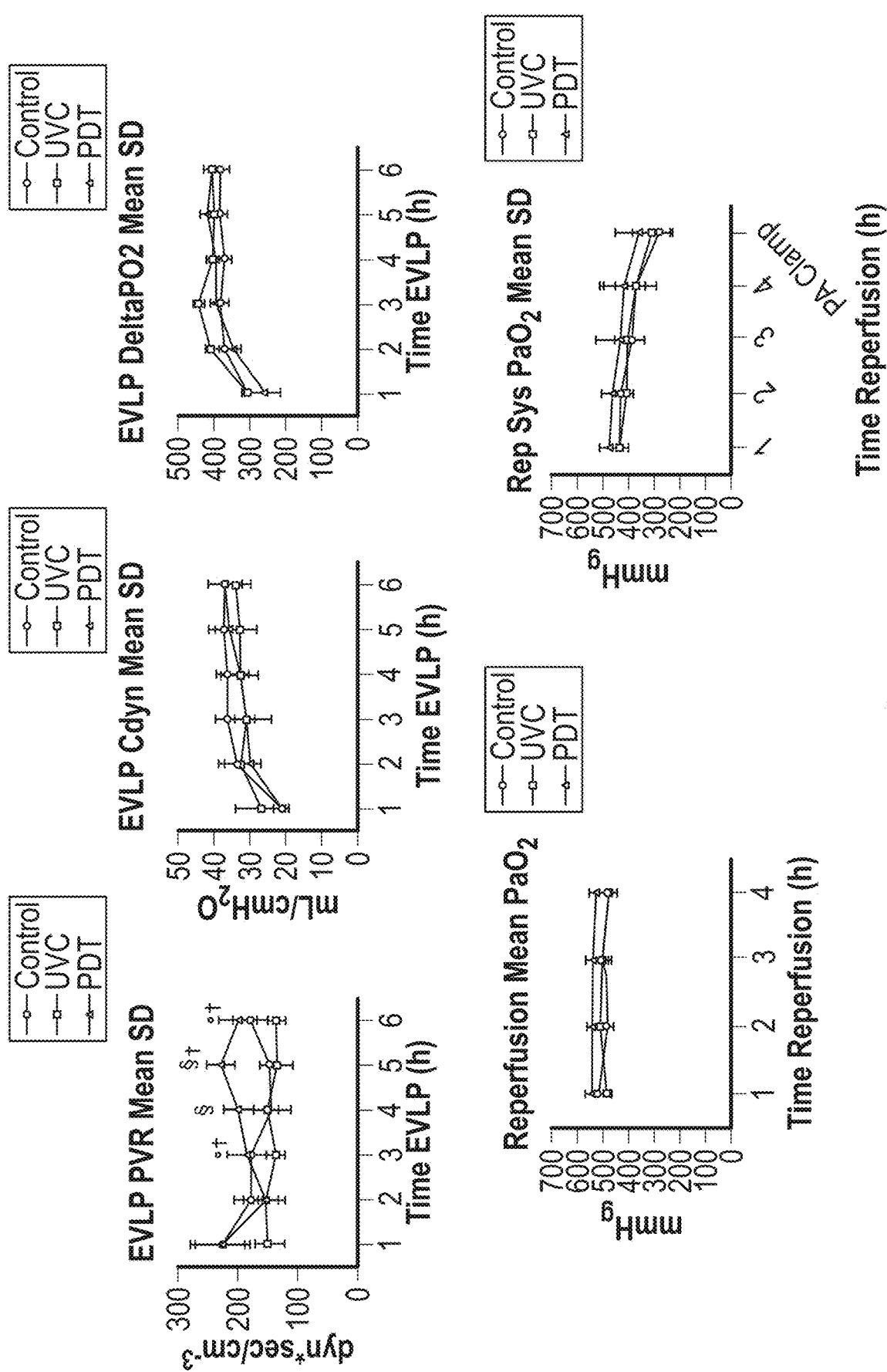
FIG. 15E is a series of graphs measuring physiologic parameters during EVLP and after transplantation.

In this model, Yorkshire male domestic pigs (30-35 kg) were used, under anesthesia and mechanic ventilation. After lung withdrawal, lungs were preserved for 2 hours at 4° C., followed by EVLP for 6 hours. During EVLP, pig lungs were randomized for three groups (n=4, each): (1) Control (standard EVLP technique); (2) Ultra Violet C; (3) Photodynamic Therapy (PDT), using Methylene Blue (MB) diluted in the perfusion solution (1 umol/L) associated with red light irradiation. During EVLP, lung physiology was assessed (pulmonary vascular resistance, pulmonary artery pressure, left atrium (venous) pressure, peak airway pressure, plateau pressure, dynamic compliance, static compliance and gas exchange function-$PO_2$); There was no difference in ex vivo lung function during 6 hours amongst the groups. After EVLP, the left lung was transplanted followed by 4 hours of reperfusion. Post-transplant blood gas samples were collected of the transplanted graft upper and lower pulmonary veins and the average of the partial pressure of arterial oxygen ($PaO_2$)/fraction of inspired oxygen ($FiO_2$) was calculated. After 4 h of reperfusion, no significant difference was found among the groups and excellent lung function was observed in all animals (FIG. 15E) demonstrating the safety of the approach during early phase of lung transplantation.

Conclusion: The effect of light-based therapies were evaluated on a donor organ. UVC and PDT during EVLP were very efficient towards virus inactivation. Pre-clinical studies demonstrated that these therapies when applied during EVLP have no demonstrable deleterious effects to the lungs. These data provide sufficient pre-clinical evidence to examine the effects of perfusate sterilization in a clinical trial using HCV positive organ donor lungs. A clinical trial using such approach will be starting to confirm the results seen It is expected that this will translate into many more good quality organs to be available for transplantation to patients suffering with end stage lung diseases.

It will of course be appreciated by those skilled in the art that many variations of the described embodiments would be possible within the scope of the invention defined by the claims herein.

The invention claimed is:

1. An ex-vivo organ perfusion system comprising:
an organ chamber for containing an organ during perfusion of the organ;
a perfusion circuit for flowing perfusate to the organ chamber; and
an irradiation system for irradiating perfusate flowing through the perfusion circuit, the irradiation system comprising:
an apparatus comprising:
a first unit comprising side panels,
a second unit pivotally mounted on the first unit such that the second unit is moveable with respect to the first unit to open and close the apparatus, and
at least one radiation source mounted on at least one of the first and second units; and
a receptacle positioned in a chamber defined by the second and first units, wherein the receptacle is a continuous tube configured for flowing perfusate through the chamber for the at least one radiation source to irradiate the perfusate as the perfusate flows through the continuous tube, wherein the continuous tube comprises an inlet and an outlet and a constant diameter body portion extending from the inlet to the outlet, and wherein each of the side panels of the first unit defines a groove adapted to support the continuous diameter body portion of the receptacle.

2. The ex-vivo organ perfusion system of claim 1, wherein the at least one radiation source comprises an ultraviolet lamp.

3. The ex-vivo organ perfusion system of claim 1, further comprising safety sensors for detecting when the second unit is moved, such that the sensors detect when the irradiator is open and/or closed and for preventing the system from being inadvertently activated while the second unit is open.

4. The ex-vivo organ perfusion system of claim 1, wherein at least one radiation source is mounted on each of the first and second units.

5. The ex-vivo organ perfusion system of claim 2, wherein the ultraviolet lamp comprises one of: ultraviolet-A, ultraviolet-B and ultraviolet-C.

6. The ex-vivo organ perfusion system of claim 3, wherein the safety sensors comprise sensing plates positioned on the first and second units.

7. The ex-vivo organ perfusion system of claim 1, wherein ends of the inlet and outlet of the receptacle are machined for fitting external tubes to the ends.

8. The ex-vivo organ perfusion system of claim 1, wherein the continuous tube is a quartz tube.

9. The ex-vivo organ perfusion system of claim 8, wherein a wall thickness of the quartz tube is between 12.6 mm and 30.2 mm.

10. The ex-vivo organ perfusion system of claim 1, wherein a joint between the first unit and the second unit bisects the apparatus.

11. The ex-vivo organ perfusion system of claim 1, wherein the first unit and the second unit comprise an equal number of the one or more radiation sources.

12. The ex-vivo organ perfusion system of claim 1, further comprising:
a male connector comprising a first tube-receiving opening configured to receive the inlet of the continuous tube to connect the inlet to the perfusion circuit; and
a female connector comprising a second tube-receiving opening configured to receive the outlet of the continuous tube to connect the outlet to the perfusion circuit.

13. The irradiation system of claim 12, wherein:
the male connector comprises a first stop-flow pin configured to prevent the perfusate from flowing from the perfusion circuit into the inlet of the continuous tube, and
the female connector comprises a second stop-flow pin configured to prevent the perfusate from flowing into the perfusion circuit from the outlet of the continuous tube.

* * * * *